United States Patent
Zhou et al.

(10) Patent No.: US 11,242,548 B2
(45) Date of Patent: Feb. 8, 2022

(54) **METHOD FOR IMPROVING YIELD AND PRODUCTION INTENSITY OF *GLUCONOBACTER OXYDANS* SORBOSE**

(71) Applicant: Jiangnan University, Wuxi (CN)

(72) Inventors: Jingwen Zhou, Wuxi (CN); Jian Chen, Wuxi (CN); Li Liu, Wuxi (CN); Weizhu Zeng, Wuxi (CN); Guocheng Du, Wuxi (CN)

(73) Assignee: Jiangnan University, Wuxi (CN)

( * ) Notice: Subject to any disclaimer, the term of this patent is extended or adjusted under 35 U.S.C. 154(b) by 173 days.

(21) Appl. No.: 16/668,637

(22) Filed: Oct. 30, 2019

(65) Prior Publication Data
US 2020/0048670 A1    Feb. 13, 2020

(30) Foreign Application Priority Data
Jan. 30, 2019    (CN) .......................... 201910089489.7

(51) Int. Cl.
*C12P 19/02*    (2006.01)
*C12N 9/04*    (2006.01)

(52) U.S. Cl.
CPC ............ *C12P 19/02* (2013.01); *C12N 9/0006* (2013.01); *C12Y 101/9901* (2013.01); *C12Y 101/99012* (2013.01)

(58) Field of Classification Search
None
See application file for complete search history.

*Primary Examiner* — Suzanne M Noakes
*Assistant Examiner* — Jae W Lee
(74) *Attorney, Agent, or Firm* — IPro, PLLC; Na Xu

(57) ABSTRACT

The present disclosure relates to a method for improving the yield and production intensity of *Gluconobacter oxydans* (*G. oxydans*) sorbose, and belongs to the technical field of fermentation engineering. By knocking out genes related to formation of D-sorbitol or L-sorbose metabolic by-products in *G. oxydans*, the formation of the by-products is reduced, and the efficiency of transforming D-sorbitol into L-sorbose is improved, thereby improving the yield and production intensity of L-sorbose. A recombinant strain *G. oxydan*-11 constructed by the present disclosure, compared with a control strain, has an L-sorbose transformation rate of 96.12%, which is 4.47% higher than that of a wild strain, has a production intensity of 14 g/L·h, which is 14.7% higher than that of the wild strain, and has a fructose by-product content of only 5.6 g/L, which is 45.6% lower than that of the wild strain.

10 Claims, No Drawings
Specification includes a Sequence Listing.

SEQUENCE LISTING

<160> NUMBER OF SEQ ID NOS: 77

<210> SEQ ID NO 1
<211> LENGTH: 2421
<212> TYPE: DNA
<213> ORGANISM: Artificial sequence
<220> FEATURE:
<223> OTHER INFORMATION: Synthetic DNA

<400> SEQUENCE: 1

```
gtgagatact taacgaatat acaaaaaaat ttatcaatta ttaccatact gtatttattt    60
attatattat tcggtttatt ggaaatttat ggaggaataa tactttttat aaatggtggg   120
tctttgtatt atataatatc aggagcactt ttggttgcgt ctggtatttt tttgcagaaa   180
agacgtattg agggtgcgtg gatatttgca ggagtatttt tccttaccct gatctggaca   240
atttgggagc gcggtttcgt ttactgggcc tggattccac gacttgatgt tcttgttgtt   300
ttggcttttg ttctgggatt tcagcttcct aaacttggac gtggcgtaaa cccagtcgtt   360
gccagatctg tttccggtgc ctccgctgcg ctgttcgggt tgggggcaat cagtgctttt   420
tatccccatt atgtaactcc tccacctgcg gattttcagg gaaaacctct ggtggatacc   480
gcggaaaccg ttacaatcca gcctgatagc gactgggata cttacgggcg tgacaagaat   540
gccacccggt tttcgcccct caagcagatc actcctgcaa atgtcggtca actgagagag   600
gcctgggttt accggacagg cgcactgaca cctgtaggtc atgccaatgc gcgcggtgct   660
gaaacgacgc ctcttaaagt cggaaatggt gtctatgtct gcacgcctct tgatgacatc   720
```

```
atcaagattg atcccgcgac gggaaagcag atctggcgcc acaattcagg aacggaatgg      780
aagaacaccc gctacgcagc cagctgccgt ggtgtaaccc actatgtttc gaccgttgtt      840
cccgttgggg agccctgtca tgagcgtatt attactggaa cactcgatga tggtcgctgg      900
cgtcttctgg cagtggatac ggaaactgga caatcctgca aggaatttgg ccaaaacgga      960
gaagtaaacc tgctggaggg aatgggacat gttgcacccg aatggttga tgaggcagcg      1020 cctcctccga tcgtaaacgg cgtgatcgtg accaatcagg aagtgatgga cggccagcgt      1080
cgttatcctc cttctggtgt aattcgtggc tacagcgccg aagatggtca attactgtgg      1140
gcgtgggacg tcaaacgacc ggatcgcaaa gggctgccgc ccgctggcga acatatagc       1200 aggggaaccc ccaattcctg gccgtcatg accggggacg agaaactggg gttggtctat       1260
gttccgacag gcaacactgc tgttgactat tacagtgcta cacgttcacc cgaagaactc      1320
gcaatttcct cttccgtggt tgcgcttgat gtgaagacag ggacagtccg atgggtgtac      1380
cagactgttc acaaggacgt atgggattac gatatcggca gtcaggctac tctgcttgat      1440
ttcccggatg cgaacggcaa ggcaatccca gggctggtta taccaaccaa gcgaggacag      1500
ctgttcgtgc ttaatcgggt aacaggtcag cccctgaccc gtgtagaaga gaaaccggcg      1560
ccgcagtatc tcgaaattcc ggaagatccg cactcgaaga cgcagccttg gtctgtcggt      1620
atgccgcggc taggtatgcc tgatcttacc gaagcaaaaa tgtggggatt gacgcctctg      1680
gatcagatat tttgccggat caagtttcgc cgtgcgcatt atgagggaga attcaccgcc      1740
cctacaatca aggaaccctg gatcgagttt cctgggaata acggtggggt agattgggga      1800
agtttggctt acgatcctac gaatggtgtt ctggtatcaa actggaacgt tgtagcaatg      1860
tataaccagc tccttcctag agcagaagcg gacaggcggg gtctgaaggc ttttgatgat      1920
ccgaactata gcccagctgt gcgtggtggc gaaggcggcg gagcacaagc tgacagtcca      1980
tatgctattg ctgtcgatgt tcttcagaat ccctttacag gtgttctttg taatgagccg      2040
ccctatggca tgatcaccgc catcgacatg catacgcaga aagtactctg ggagcgacct      2100
cttggtacag ctcgggcaaa tggtcctttc ggtttgaaga cctatgctcc agtagagttc      2160
ggcgtcccca gtaatggtgg tcccatgatt accgcaggtg gtctggtctt tatcgccgcc      2220
gctacggata acttgatccg ggccattgat atcaagacag gaaaaattgt ctggcatgcc      2280
attctaccgg caggcggaca ggcgacgcca atgacctatg aagtcaatgg ccagcaatat      2340
gttgcgatcg ttgcgggagg acatcattat atgaacacgc atgatggtga ttatgttatc      2400
gcctatgcac ttccgaaata a                                               2421
```

<210> SEQ ID NO 2
<211> LENGTH: 756
<212> TYPE: DNA
<213> ORGANISM: Artificial sequence
<220> FEATURE:
<223> OTHER INFORMATION: Synthetic DNA

<400> SEQUENCE: 2

```
atgagtacct ctcttttga tctgaccggc cgccgtgccc ttatcaccgg ctcgtctcag      60
ggcattggtt tcagtctcgc gcaaggcctt caggcagccg agccgacat cgttctcaat       120 ggtcgtgatc cagaaaaact cagtattgcg gctgagaaac tgggtggggt gaaaacgctg      180 cctttgacg tcacggatca tgctggggtc aaagctgcga ttgatcgctt tgaagctgaa       240
acaggcccga tcgatattct tgtcaacaat gctggaatgc agcatcgggc gccgctggaa      300
```

```
gattttccgc cggaaatgtt tcagaaggtt ctccagacaa atctgacctc catcttcaat    360
gttgggcagg cagtcgcaaa acatatgctc ggccgaaaga gtggcaagat catcaatatc    420
gcgagcgtgc aaacagccct cgcccgcccg aacatctcgc catacaccgc gaccaaaggg    480
gcggttggta atctgacaaa gggcatggcc acggaatggg caaggcacgg tctgcaatgc    540
aacgcgatcg cgccagggta ttttgatacg cctttgaatg cagccttggt caaagacgct    600
gacttctcac aatggctgga aaagcggacc cctgccgggc gatggggaca attggacgaa    660
ctgaccggag cttgtatctt tctggcgtcg caggcttcgt ccttcgtaaa cggccatgtt    720
ctgtatgtgg atggcgggat tacggtctct ctttga                             756
```

<210> SEQ ID NO 3
<211> LENGTH: 1044
<212> TYPE: DNA
<213> ORGANISM: Artificial sequence
<220> FEATURE:
<223> OTHER INFORMATION: Synthetic DNA

<400> SEQUENCE: 3

```
atggctcaag ctttggttct ggaacgtaaa ggcgaactgt ccctccgaga gattgacgtg     60
cctgatgtcc tcggccctga tgacgtcagg gtagcgatcc atacagtcgg tatctgcgga    120
agtgatgtcc attattatac gcatggacgc atcggtcatt tcatcgtaga cgctccgatg    180
gttcttggcc atgaggcctc aggcaccgtg acggaagttg gttcacgcgt aacaagtctt    240
caggttggcg atcgtgtctg catggagcct ggcattcctg accccacctc acgcgcgtct    300
aaaatgggta tttacaacgt tgatcctgcc gtaactttct gggcgacgcc gccaattcat    360
ggttgcctca cccctcggt cgtacaccca gcggccttta cttacaggct tcctgagaat    420
gtttcattcg ccgaaggcgc catggtagag ccattcgcta ttggcgttca ggcagccgtc    480
aaagccgccc tgaagccggg cgatacatgt ctagtcacgg ggtgtggacc gattgggctt    540
atgacagcac tggcagcact ggcttcaggg gcaggaacag ttttttattc cgatatcgcc    600
gctccgaagt tgcagatcgc tggacaatat aaaggtctcg ttcccttgaa cgctaaagaa    660
gtacggccac gcgatgcggt gtcgcagcag tgccgagcgg actggggtgt tgatgttgtt    720
ttcgaggcca gcggctttcc gggggcatat gacgatgtct tttcctgcgt ccgccccggt    780
ggaaccgttg tgttcgtcgg aatgcctgtc gagaaggtcc cgtttgatct ggtcgcagct    840
caagccaaag aaatccgaat ggaaacagtc ttcaggtacg cgaatgtcta tgaacgtgcc    900
attgccctga tttcttcagg aaaagtggat ctcaagcccc ttatttctga aacgtttcca    960
tttgcagaag gtatcgcagc ctttgaacgc gcggcttccg ctcgtccaac ggatgtgaag   1020
ctacaaatta agcttccagg ctga                                         1044
```

<210> SEQ ID NO 4
<211> LENGTH: 1539
<212> TYPE: DNA
<213> ORGANISM: Artificial sequence
<220> FEATURE:
<223> OTHER INFORMATION: Synthetic DNA

<400> SEQUENCE: 4

```
atgtgtctgc acaatcgcca gaaagacagg gagaagccgt ccatgaacaa gatggcacag     60
aaactggctc catccggagt tgctcgtgac tttggatttt tcatcgatgg tgagtggcgc    120
cacggacgtg agatgttcga gcgcaaatct cccagtcatg atgttgtagt cacgcggatt    180
gcacgttgca cggaagagga tctgaacgac gcagtggctg ctgcccgccg tgcgtttgaa    240
```

```
aacggcacat gggctggtct ggcaagttcg gaacgtagtg cgatcctgtt gaagacggca    300
gaactgctga agcagcgccg cgacgatatt gccttctggg aagtgctgga aaacggcaag    360
ccgatctcac aggccaaggc cgagatcgac aactgtattt cctgtttcga gatggctgcg    420
ggtgccgcac gtcttctgca tggagacagc tttaacaatc ttggcgagag cctgttcggc    480
atggttctgc gggagccggt cggggttgtt ggcctcatta cgccctggaa cttcccgttc    540
atgatcctgt gtgagcgcgt gccattcatt ctggcatccg gctgcacagt tgttgtgaag    600
ccagcggaag tgaccagcgc caccacgctg atgctcgccg atattctgac agaagctggc    660
ctgccaaagg cgtcctataa cgtcgtaacc ggcacgggca aaagcgttgg gcaggccctg    720
acgcagcatc cggatgtaga catgctctcc ttcaccggct ccaccggggt tggccggtcc    780
tgcattcatg cgtccgcaga cagcaacctc aagaagcttg gcctggagct tggtggcaag    840
aacccgatcg tcgtcttcgc ggatagtgat ctggaagatg cggccgatgc ggtggccttc    900
gggatcagct tcaacaccgg gcagtgctgc gtctcgtcca gccgcttgat tgtcgaagag    960
tccgtggccg acaagtttga gaagctggtt gtcgccaaga tggaaaagat ccgcgtgggt   1020
gacccgttcg acccggaaac gcagattggc gccatcacaa cggatgcgca gaacaaaacc   1080
attcttgatt atattgagaa gggtaaggcc gaaggcgcgc gcgttctgtg tggtggcaac   1140
aaggtcgatc tgggtcgtgg gcagtacatc gcgccaacgc tcttcacgaa tgtgaagccg   1200
gacatgtcga ttgcgacaga cgaaatcttt ggtcctgtgc tgtcagtctt ccggttcggc   1260
acccttgaag aagcgatctc cctggccaat gacacggctt atggtctggc ggcgtctgtc   1320
tggacgaagg acatcagcaa ggccctcaag gtgacacgca aggttcaggc cgggcgcttc   1380
tgggtcaaca cgatcatggc tggcggcccc gaaatgccgc tgggtggttt caagcagtcc   1440 ggctgggggcc gtgaagcggg gatgtacgga gtggaggaat acacccagat caaatccgtt   1500
cacgtcgatc tcggtaaacg gacgcactgg atctcctga                          1539
```

<210> SEQ ID NO 5
<211> LENGTH: 495
<212> TYPE: DNA
<213> ORGANISM: Artificial sequence
<220> FEATURE:
<223> OTHER INFORMATION: Synthetic DNA

<400> SEQUENCE: 5

```
atggctcagg cactggtgtt tgaaaggaga ggtgaactct ctctacggga gatcgccctt     60
ccgtcggagc ttggaccgga tgatgtccgt atcgccatcc atatggtggg tatctgcggc    120
agcgacgtgc attactacac gcatggtgcc attgggccct tcgttgtttg tgagcccatg    180
gtgctgggac acgaagcctc tggaacaatc actgaagtcg gaagccatgt ccggtctctg    240
aaggtcggag accgggtgtg cagggagccg gtatcccag acccacaatc ccgtgcaacg    300
ctgatggttc ggtacaccgt tgatcctgct gttcgcttct gggcgacccc gccaatccac    360
ggctgtatca gtgcagggaa aatcgatctc aagccgcttg tgtcggaaac attcccttttt    420 gatcagggta ttgccgcttt tgaacgggct gccgaggctc agccgagcga cgtcaaactc    480
cagatcgttc tctga                                                     495
```

<210> SEQ ID NO 6
<211> LENGTH: 3487
<212> TYPE: DNA
<213> ORGANISM: Artificial sequence
<220> FEATURE:

<223> OTHER INFORMATION: Synthetic DNA

<400> SEQUENCE: 6

```
atggatcggg aaaaagtcca tcctctcatc gggcaggccc tctacgacac tcttttgtct      60
caaagagcag cctaccgaag tgagatcaat caactgcatg atcttctcac tacaaaagag     120
tttagttcag ccgccgaatt tgcccgtgag gccgagcatt ctgacaacgc gctgaaagag     180
accattcatg ccctgatgca cggctggtat cggggcgtcg tgggtcagac agtcgtcgtc     240
taccgtgcgg ccgccatgtt tgctctgact gatgatgcgg tctttcccaa gacttatgcg     300
acagcgagac ccttctactg gactgaaaag ccgccagtcg ttgagacgcc aacagcggcc     360
ccggcactgt ctccatcgga atatgtcgca gaatcccagt aagaaacgga tgttatttca     420
atgagttctt cgaattccct ttcggcagat gtcgtgatcg tgggatccgg cgtcgcaggg     480
gccagtattg ccaacgaact tgcgagagcc ggcctctccg tcatcgttct tgaagccggc     540
ccccggatcg accgccagca tattcttgaa aatttccgca ccacggaaaa caagggagca     600
taccagcttc cctacccacc cgtgccttgg gcgatgcatc cgcctgatca gggctctccc     660
aatggctatc tgcatacgac cggacctgac ggtgctgcgt atcagcaggg ctatctgcgt     720
gttgtcgggg gaacgacctg gcattgggca ggatgtgcct ggcggtatct cccctctgac     780
ttcgagttac attccgata tggcgttggc cgcgactggg ccatcaagta cgatgatctg     840
gagccattct actatcaggc cgaagtcatg atgggcgtgg caggccctaa catggatgtc     900
gatgacctgg atctccacg atctcacgat tacccgatga aggaagtacc cctgtcctat     960
ggcgcggatc agtttcgcaa actgatccat gagaagacga attaccgcgt cgttcacgag    1020
ccacaggccc gtaacactcg cccttatgac aagcgcccaa cctgtgaggg caacaacaac    1080
tgcatgccga tctgtccgat cggggcgatg tacaacggaa ttcactcggt caatcatgcg    1140
gaagcagcag gcgcccgtat tattccgaat gcggttgtct accgactgga gaccgacgcc    1200
agcaacaaga aggtcgtggc cgtaaattat tacgatcccg ataagaattc tcatcgtgtc    1260
accggtaagt tcttcgtggt cgctgcgcac tgcattgaga gtgccaagct gctcctgctg    1320
tccgccgatg acaaaaatcc ccggggcatt gccaacagtt cagatcaggt tggtcggaac    1380
atgatggatc acacgggcgt acagctctcg tttatgagcg gaaacgactc tctgtggccg    1440
ggtcgtggtc ctctgctgac cagcattatc gactcgtttc gtgacggccc atggcggagc    1500
gaacgtggtg cgtatcttgt gcatatggtt gacgataatc aggtcgactt cgcaacgggt    1560
ctggcgattg ccaagggcta tgtcgggaaa gagctggaag agcagatccg ttatggctcc    1620
tctcatgccg ttcgtctctt cagccataac gaaggcattg ccgaccccga caaccggctg    1680
acactgagca aaacacataa agacgttctg ggcattcctc accccgaagt ctattacaag    1740
cttcccgagt acacagtgaa gagttgtgac cataccaagg agctgttcaa ggaactgatg    1800
gctctgatga gtggtactga tcctcaatgg acaaagggtt acttcccgca gtgccatccg    1860
tcgggcagca cgatcatggg aacagacccc accaattcgg tcgttgacgg tgagtgccgc    1920
acccatgacc acgaaaacct gtttgttgcc agttcagcgg tcttctcttc ggtcggtaca    1980
ggcaatatca ccctgaccat tgccgcgctg gcgcttcgcg ttgcagcatc cctgaaaaag    2040
gagatgcttc atgcgtgagg ggaataaagc cggaatacgc cgcctctttc tgccagctgc    2100
catagcttcg ggtgtcctgt tcggcgcgca gtcagcgagg gcagaggatc aggccaccac    2160
tatcagccga ggcgcctatc tggctacagc aggcgactgc gttgcctgcc atacgaaacc    2220
aggtggggct ccctttgcgg gcggccttgt cattgcgtcc ccaatgggcg ggatcgtcgc    2280
```

```
gtccaacatt acacccgatc cggatacggg aattggcaaa tacaccgaag aggagtttgc    2340
caacgctctt cgcaagggta ttcgcaggga cggagctcat ctctatccgg ccatgcctta    2400
cacggcctat tcggagattg cggatacgga catccacgca ttgtatgtct acttcatgca    2460
tggcgtggcc cccctgcagc aggacaatcc gaagacggga ctgaaattcc ccttcaatat    2520
ccgcgcaatg atgatcagct ggaatctcct gttcgcagga cctccggccg caaagggtga    2580
tcctcagacc tattccaaaa tcgaaagagg ccactatctc gcagatgcct gggacattg     2640 cggaacctgt catacaccac gcaatttcct gatgggcgaa cgcagcagca gtgcctatct    2700
tggcggaacg ccgctcgctg gctggtatgc tcccaacatc acaccgagca tgaatagcgg    2760
gatcggcgat ggagcgaag acgatctggt tcagtacctg cgtacaggct ccgtgccagg     2820
acgtgctcag gcggcaggca tgatgggcga agctgttgaa catagcttta gcaagctgac    2880
agacgaggat ctccacgcga tcgccgccta tatccgacag atcccaaaga tcgaggacag    2940
ccaagcaaaa cagccgcgtg accggttcgg ggttgccgtc cagcccatcg tggatctgca    3000
gaagccaaaa cttgatcgtg aagatgacct gtttccgatg gacggggaga ggatctacgt    3060
caacaactgt gcagcctgcc atggacttga tggtgcagga cggccgatc acttcacgcc     3120 ctctctgtcc tccaatgcag tagtcggtgc accgggagct gacaatctga tcatggccat    3180
tgtcaacggc gttgatcgca cgacgaatgg tcatcacgtt ctgatgccgg tttcggccc     3240 cacttccgat gtacaacggc tcagcgatac ggatgtggcg aaactcacca actatgtctc    3300
cgggacattt ggaagtggcg atcatcatgt cacagctcag gacgtaaagg tcgctcgtga    3360
aggcgggcct ctgccagcac tagtgaagga tatgccggcc ttaattgggg ctggtgttat    3420
tgcagccttt gcagcaatgt catgcctgat ctggtggttc agacggcgca ctcaaaaaca    3480
gaaataa                                                              3487
```

<210> SEQ ID NO 7
<211> LENGTH: 969
<212> TYPE: DNA
<213> ORGANISM: Artificial sequence
<220> FEATURE:
<223> OTHER INFORMATION: Synthetic DNA

<400> SEQUENCE: 7

```
atgacaccgg tgaatattcc cgagtccgaa cctttggcag atatggtcc tggttccaga      60 cagatcctga tcgttacagg gctttccggt gccggaaaat catccattct acgtgtgctt    120
gaagatctcg gctacgaagt cgtggataat ccacctttgc accttcttga agccctggcc    180
tcacgaagca tctcccgact ggccattgga atcgatgtcc gaagtcgtgg ctttgaagcg    240
tcccgtgttc ttgaggaaat ggaccggctg aaagctctcc ctggcagtca ggttcagctt    300
ctctatgcaa cggccgagcc tgaaatcctg ttgcgtcgct ttacggccac ccggcgtcgc    360
catcctctgg ttacgagcgg cacgatcctt ccgggtatcg agcaggaaag tcgtctgctg    420 gccccttgc gtgcccatgc ggattttgtc atcgatacat cggacttgcc cgcccctgaa     480
ttgaggcagt tgatcgagac ccgtttcggc agtggctccg aagatggtct gactgtcgcg    540
cttatgtctt tcgcttatcc atccggcctg ccgaggaag cggatatggt attcgatgcc      600
cggttcctgc gaaatccaca ttatgacccg acgctacaac ccatgacagg tctggatcag    660
gcggtcgtga agcacgtcaa gcaggatccg gcttatccgg ccttcttcaa tcatgtgcat    720
ggcctgctgg atctcgtgct gccccgcttt gttgaggaag gcaaaaaata cgccaccatc    780
```

| | |
|---|---|
| gctgtagggt gcagcggtgg ccgccaccgt tctgtcacca tcattgagga actggcgcgt | 840 |
| ctgctgccag aaacggcgcc tgttggcccg atgatggtgc tgcatcgtga gctggcgcgg | 900 |
| aaaggcctgt cctcttggcg ttgggctgtt ccgccgcata acctgtcccc gcaggacaaa | 960 |
| tctgcatga | 969 |

<210> SEQ ID NO 8
<211> LENGTH: 2430
<212> TYPE: DNA
<213> ORGANISM: Artificial sequence
<220> FEATURE:
<223> OTHER INFORMATION: Synthetic DNA

<400> SEQUENCE: 8

| | |
|---|---|
| atgccgccta cgttgcgacg cagttcgttc ctgccccttg tgacgggcat cttgctcgtt | 60 |
| ctgctcggcc tagggctggc tttacccggt ctgtggttaa ttgggctggg aggctctttc | 120 |
| tactacgcca ttgcaggcgt tctcatggtg gcatccggcg ttctgatgat ccggctgcac | 180 |
| cccggcgctt ccgcagttta tgcagggctc ctgctttata cgcttgtctg ggcattaggg | 240 |
| cgtgttggcc ttgatggctg gcgccttctc ccgcctctcg cgctgccagc aggaatgggc | 300 |
| ctctgggtgt tcagccccctg gattacggga cgactgctcc agggcacgaa acatcgttcc | 360 |
| gtcagcatac ccgttgttgc aggtggcatg gcattctgcg cggcattgtt tgtctttgtg | 420 |
| ttcgcctgcg gttggcacat tactgcatca cgcgaccagc agttcaatcc gttccccggt | 480 |
| gagaccggtg cgacccttcc gggcgcggat cagcaggctg ccaatgactg cagttctat | 540 |
| ggtggcactc cggccggaga ccgctttgcc atgccaaccc agatcaatgc ttccaacgct | 600 |
| cacggtctga agtagcgtg ggtgtatcac agcaaggatc tgccgcgcgc tggcgagaac | 660 |
| tcccgtgggc gggaattcag ctttgaagca acgcccatca aaatcggcaa ccggctgttt | 720 |
| ttctgcacgc cgcaccgaga tgtcgtggcg ctggatgcaa catccggaaa ggaaatctgg | 780 |
| cgatattcgc cggtggaga attcggcaag aacatctatc aggcctgccg cggcgtatcc | 840 |
| tacgtcaatg ctccgggaac ggattacgcc catcgcatcg tctcaacaaa ttccagctcc | 900 |
| cctccaaccc tgtttgaagt cgatgcagac acgggaaaac tctgcgaaag ctttggcgat | 960 |
| catggtgttg tggatctccg gggtgggatg ggagctattc cacccggctt tcacttcatc | 1020 |
| acgtccccac ccatggtgct gcataaccgt atcatgacga gtggctgggt ttatgatgat | 1080 |
| cagacagttg gcgaaccttc cggggttatt cgtggcttcg atgccattac gggccaactg | 1140 |
| gcctgggcct gggacatggg ccgcaccccg accaacaaac ctctggatcc gggcgaagtc | 1200 |
| tttacccgtg gcaccgccaa tggctggggc gtctatacgg ccgatgccgg gctgaacatg | 1260 |
| gtttacgtcc cgctcgggat tgccacgcct gactatttcg gtggcaaacg ccggagcttt | 1320 |
| gacgagaagt atgacagctc tctcgtagcg ctggacatca caacgggcga agagcgctgg | 1380 |
| catttccaga ccgttcatca tgatctgtgg gattttgatc tccccgttgg cccatctttta | 1440 |
| gtggatctgc cagatgccca cggcactctg accccgcgc tggtacagac aaccaagcag | 1500 |
| ggcgaactct tcgtgctgga ccgccgaacc ggcgcgccat tctatcgcgt tcaggaaaca | 1560 |
| cccgtacctg ccggggacac gccgggcgag cattattcgc cgacgcagcc actctccgtc | 1620 |
| gacatgccca atctgcgccg ccccaatctg acggaagacg atatgtgggg cgcgaccccg | 1680 |
| tatgatcaga tgttctgccg tattgccttc cgctccatgc gggacaatgg ccttttcaca | 1740 |
| ccgccgagcc agaaaggcac cgtagggttt ccagcgtttg atggcgtggc ggactggtat | 1800 |
| ggtggcacca tcgatccgac gcatggtgtc atgtatatca acaccacgtt cattccattc | 1860 |

| | |
|---|---:|
| ctgatgacgc tggtgccgca ggaaaaagct cttgccaaag ggctctacaa atcctggcgt | 1920 |
| gactgggcac agccttatcc ggagcctgtt ttcacaaaca atccccaaca tggcctgccc | 1980 |
| ttcgcggctg tcgtgaagcc atggcttggc ccgtttggcg ctccgtgcct ggcaccccca | 2040 |
| tggggcaaga tgcaggcgat tgatcttgtt catcgtcggg tcatctggga acgggctttg | 2100 |
| ggcacaacga agaatgttgg cccgacaaac atgctgcgga tgcccgttgg cctccccacc | 2160 |
| agtgtcttct ccatgggcgg cagcgtgacc acgccgaatg tctggtgtt catgggcgcg | 2220 |
| ctggcggatc aaagcttcca tgttcttgat gggcatgacg ccatacgct cttcaagacg | 2280 |
| gaactggacg ccggcggcaa tgccacgccg ttgacctata tgggtgaaga cggccggcaa | 2340 |
| tatgtcgtgc tggctgtggg cggccacggt gggctaaaaa cgcgcaacag cgatgaagtc | 2400 |
| gtggcctttg cattacccaa agccccatga | 2430 |

```
<210> SEQ ID NO 9
<211> LENGTH: 1467
<212> TYPE: DNA
<213> ORGANISM: Artificial sequence
<220> FEATURE:
<223> OTHER INFORMATION: Synthetic DNA

<400> SEQUENCE: 9
```

| | |
|---|---:|
| atgatcatca atgggatttt ccttcctttc ccctctttg tcctgtcagt ggggacaatg | 60 |
| cttctgcttg catcagtcac gctgcatcga tcgtccagac tcagtttctc tctggggctg | 120 |
| ctaacgctcg ttcttgcaac cgtgatgacc tattatcctg cccccatcat gcctcttgcg | 180 |
| gccacgcaga cactcttctt cgcagataca tgggccaact acacagccgc tctgatttta | 240 |
| ctctccgcat cctgcatctt cattctttcc tggcaggacg tgacccagcg cagcgccccgg | 300 |
| tcggcagacg aatacgccct cctcctactc cttggtgcgt tggggctac ggccatggta | 360 |
| ttcagtgtaa actacatgcc gttttcctt ggggtggaaa tactctccat tgcattgatt | 420 |
| ggactggtga cattcaggag ccgacacacc cagaaaggcc tggaagcggc gatgaaatac | 480 |
| ctgatcctgt caggtgttc atcagccatt cttctctttg tatcgggtt gtcctattcc | 540 |
| gtcaccggat ccttggtttt cgaattttcc accgcgggtc atgaaacggg cacaggtatt | 600 |
| gctgccgctg caagcataat ggttctgacc ggaattttct ttaagctctc cgctgtaccg | 660 |
| ttccatatgt ggattctcga cgtcatggag ggggcatctg tccctattgc cggtttcata | 720 |
| gccgtcgttc ccaagattgg tatattttct gcgctggtgc ggtatttcgg ttctgaaccc | 780 |
| gtcacgcctt tcctgcataa tacaatgtca gccatcatta ttctgaccat tctgggtgga | 840 |
| aatctgcttg cgctttgcca gaccagtctg atcagactga tggcgtgttc atccatcgcc | 900 |
| catgtaggct atctgctcat tgcattctat tcacctggtc atttccagtc tgatacaatg | 960 |
| gtgctctatc tggctgccta taccgcagcc acactgggta cttttctcga tatccaggct | 1020 |
| ttcgtaagtc cagaagggct gcagcgcagc acgatttctg actggaaagg actgttttt | 1080 |
| acccatccct ttctcgcggt cgcaatgact gccatgctgc tttccctcgc aggtattcct | 1140 |
| cccacaattg cttttttgc caaatttgaa attgccgctt caggtctgga gcaaagacat | 1200 |
| tatatccttc tcacagcgtt aattgtcgga agcatcatag ccttatatta ttatctcaat | 1260 |
| attataagat taatgacaac accaaacact tccttaaata ttggacaaaa tgagaaaaca | 1320 |
| aatttaataa tttacagtac tgtttttatt ttaacattaa tcgtgtttgt aggaggaatt | 1380 |
| tttccttcat ttttatgaa ttccatacat ccggctcttc catcgacaag agctgaatat | 1440 | cttcaaagcc acattccatt accttga                                        1467

<210> SEQ ID NO 10
<211> LENGTH: 1164
<212> TYPE: DNA
<213> ORGANISM: Artificial sequence
<220> FEATURE:
<223> OTHER INFORMATION: Synthetic DNA

<400> SEQUENCE: 10
atgatggatt tttccttctt caatcctaca cgcgtactct ttgggcgcac agcactgtcc      60
caaatgacgg cccttgttcc ggcaggagcc cgaattctca ttctttatgg cggtggaagc     120
gtcgtacgca acggaacgct tgcacgcgtt caagctgcgc ttgacgggta tgaaattcat     180
gagttcggag gcatcgaacc caatccgagc tttgaaaaac tgatggaagc cgtgacattg     240
gtgcgagagc aggacatcag tttcctgatc gccctcggcg aggatccgt gatcgacggc      300
gcaaagtttg tggccgccgc agtttactat gatggcgatc cctgggacat tcttctgacg     360
cgtggcaatc ggatccaggc tgccctacca ctggccgcta ttccgacact gcccgcgacg     420
gggtcggaaa tgaacggaac atcggtaatt acgcggaccg aattttccgc caagcgtgtg     480
ttcaagagcg agcatgtttt ccccgttctg gcggttctcg atccgacatt gacgttcaca     540
ctgccgcccc gacaggtcgc caacggaatc gtcgatgcgt tcgtccatgt cctcgaacag     600
tatctgacct atcctgtgga tgctcctgta caggatcggt tgcagagggg cctgctacgc     660
gtcctccttg acgttgccga caaaaatctt gccgagcctg aaaactatga tgcccgcgcc     720
tccctgatgt gggccgcaac gctggccctc aatggcctga taggatcagg cgtgccgcag     780
gactggtcca gtcacctgat cggacatgaa ctgacggctt tgtacggcct cgaccatgcc     840
cgcacactcg ccgtcattct gcctgccatg ctatccgtgc ggaaaagcga aaagcatgcc     900
aaactgcttc agtatgccga gcgtatttgg aatctccaca ccggctccga aaacgagcgg     960
attgataagg ccctgagtca cacgagggct ttttcagcc atctcggtct ggaaaccggt     1020
cttttcagatt atgggctggg ccggaacgct attgactctc tgctcgcatc cctgcggcag    1080
gctcacggaa atgattatgc ccttggtgaa aagcagactg tctcttcgga gcttgccaga    1140
gccgttctgg aggctagtct ataa                                           1164

<210> SEQ ID NO 11
<211> LENGTH: 639
<212> TYPE: DNA
<213> ORGANISM: Artificial sequence
<220> FEATURE:
<223> OTHER INFORMATION: Synthetic DNA

<400> SEQUENCE: 11
atgagtcagg cgctgccgcc tatcgttctc acccatccgc tggtgcgcca caagctgacc      60
cgtctgcgtg ataagaacac atccacagcg ggctttcgtc gcctgacccg tgagctcagt     120
ctgcttctgg cttatgaagc cacgcgtaac ctgtctctcg tgccacgtca gatcgaggcg     180
ccaagcgggt tgatggaagg tgaggaactg gacggcaaga agctttgctt cgtctccatt     240
ctgccgtgccg gtaacggcct tctggacgga atgctggatc tcgtaccgtc tgcgcgtgtg    300
gggcatatcg ggctgcggcg cgaccatgag acgctggaag tcagcgaata ctatttcaat     360
atgccgagcg atgttccggg ccggacctgc atcgttctgg accgatgct ggccaccggg      420
cactcggctg ccgctgctgt aacgcgcgtc aaggaagcgg gagcgattgc gcctgttttt     480
gcctgccttc tggcggctcc ggaaggaatt gctcacatga cggaactgca tccggatgtg     540

```
caggtcgtga cgtgttgtgt ggatcagaag cttgatgagc acggctatat tgtcccgggt    600
ctgggcgatg ctggcgaccg tctgttcggg acccgctaa                           639

<210> SEQ ID NO 12
<211> LENGTH: 23
<212> TYPE: DNA
<213> ORGANISM: Artificial sequence
<220> FEATURE:
<223> OTHER INFORMATION: Synthetic DNA

<400> SEQUENCE: 12
gacgcccctc agatcgacac ggt                                             23

<210> SEQ ID NO 13
<211> LENGTH: 24
<212> TYPE: DNA
<213> ORGANISM: Artificial sequence
<220> FEATURE:
<223> OTHER INFORMATION: Synthetic DNA

<400> SEQUENCE: 13
cagagctttt cgggctgcct gtac                                            24

<210> SEQ ID NO 14
<211> LENGTH: 53
<212> TYPE: DNA
<213> ORGANISM: Artificial sequence
<220> FEATURE:
<223> OTHER INFORMATION: Synthetic DNA

<400> SEQUENCE: 14
attccaccgc cgccttctat gaaaggaacc tcagattttc tggagactga cca            53

<210> SEQ ID NO 15
<211> LENGTH: 52
<212> TYPE: DNA
<213> ORGANISM: Artificial sequence
<220> FEATURE:
<223> OTHER INFORMATION: Synthetic DNA

<400> SEQUENCE: 15
cgaggaagcg cctgaaaaca ttgtcttaac cggccataaa acggcatggt at             52

<210> SEQ ID NO 16
<211> LENGTH: 52
<212> TYPE: DNA
<213> ORGANISM: Artificial sequence
<220> FEATURE:
<223> OTHER INFORMATION: Synthetic DNA

<400> SEQUENCE: 16
taaacggacg cactggatct cctgatgagg tatttggaat gagtcgccgt ca             52

<210> SEQ ID NO 17
<211> LENGTH: 50
<212> TYPE: DNA
<213> ORGANISM: Artificial sequence
<220> FEATURE:
<223> OTHER INFORMATION: Synthetic DNA

<400> SEQUENCE: 17
gtcagtctcc agaaaatctg aggttccttt catagaaggc ggcggtggaa                50

<210> SEQ ID NO 18
```

```
<211> LENGTH: 22
<212> TYPE: DNA
<213> ORGANISM: Artificial sequence
<220> FEATURE:
<223> OTHER INFORMATION: Synthetic DNA

<400> SEQUENCE: 18
gcagcccaac ccagccgatg at                                               22

<210> SEQ ID NO 19
<211> LENGTH: 24
<212> TYPE: DNA
<213> ORGANISM: Artificial sequence
<220> FEATURE:
<223> OTHER INFORMATION: Synthetic DNA

<400> SEQUENCE: 19
cattctttca agggcgcaga ccat                                             24

<210> SEQ ID NO 20
<211> LENGTH: 24
<212> TYPE: DNA
<213> ORGANISM: Artificial sequence
<220> FEATURE:
<223> OTHER INFORMATION: Synthetic DNA

<400> SEQUENCE: 20
ccttcaatat ggtacgcgct cctg                                             24

<210> SEQ ID NO 21
<211> LENGTH: 24
<212> TYPE: DNA
<213> ORGANISM: Artificial sequence
<220> FEATURE:
<223> OTHER INFORMATION: Synthetic DNA

<400> SEQUENCE: 21
agctgtaacc attcaaggct ggcg                                             24

<210> SEQ ID NO 22
<211> LENGTH: 38
<212> TYPE: DNA
<213> ORGANISM: Artificial sequence
<220> FEATURE:
<223> OTHER INFORMATION: Synthetic DNA

<400> SEQUENCE: 22
agcgcgtacc atattgaagg tggcggatcg gcgtaacg                              38

<210> SEQ ID NO 23
<211> LENGTH: 42
<212> TYPE: DNA
<213> ORGANISM: Artificial sequence
<220> FEATURE:
<223> OTHER INFORMATION: Synthetic DNA

<400> SEQUENCE: 23
agccttgaat ggttacagct cgtgtttctg cggtgtggtg ac                         42

<210> SEQ ID NO 24
<211> LENGTH: 23
<212> TYPE: DNA
<213> ORGANISM: Artificial sequence
<220> FEATURE:
<223> OTHER INFORMATION: Synthetic DNA

<400> SEQUENCE: 24
```

-continued gaaaagatcc cggacagatt ggc                                               23

<210> SEQ ID NO 25
<211> LENGTH: 24
<212> TYPE: DNA
<213> ORGANISM: Artificial sequence
<220> FEATURE:
<223> OTHER INFORMATION: Synthetic DNA

<400> SEQUENCE: 25
cgtagttggc cgtcaggttg aaat                                              24

<210> SEQ ID NO 26
<211> LENGTH: 24
<212> TYPE: DNA
<213> ORGANISM: Artificial sequence
<220> FEATURE:
<223> OTHER INFORMATION: Synthetic DNA

<400> SEQUENCE: 26
ggaagtcgcg caatgatcat gtcc                                              24

<210> SEQ ID NO 27
<211> LENGTH: 24
<212> TYPE: DNA
<213> ORGANISM: Artificial sequence
<220> FEATURE:
<223> OTHER INFORMATION: Synthetic DNA

<400> SEQUENCE: 27
agaatttcag ccgtcatagt ggtg                                              24

<210> SEQ ID NO 28
<211> LENGTH: 38
<212> TYPE: DNA
<213> ORGANISM: Artificial sequence
<220> FEATURE:
<223> OTHER INFORMATION: Synthetic DNA

<400> SEQUENCE: 28
atgatcattg cgcgacttcc tggcggatcg gcgtaacg                               38

<210> SEQ ID NO 29
<211> LENGTH: 42
<212> TYPE: DNA
<213> ORGANISM: Artificial sequence
<220> FEATURE:
<223> OTHER INFORMATION: Synthetic DNA

<400> SEQUENCE: 29
actatgacgg ctgaaattct cgtgtttctg cggtgtggtg ac                          42

<210> SEQ ID NO 30
<211> LENGTH: 22
<212> TYPE: DNA
<213> ORGANISM: Artificial sequence
<220> FEATURE:
<223> OTHER INFORMATION: Synthetic DNA

<400> SEQUENCE: 30
agtcacctga tctggattgg cg                                                22

<210> SEQ ID NO 31
<211> LENGTH: 22
<212> TYPE: DNA

```
<213> ORGANISM: Artificial sequence
<220> FEATURE:
<223> OTHER INFORMATION: Synthetic DNA

<400> SEQUENCE: 31
ttccatgcaa gagaagggga cc                                              22

<210> SEQ ID NO 32
<211> LENGTH: 22
<212> TYPE: DNA
<213> ORGANISM: Artificial sequence
<220> FEATURE:
<223> OTHER INFORMATION: Synthetic DNA

<400> SEQUENCE: 32
tcctgcaatg cctcaatcgt tc                                              22

<210> SEQ ID NO 33
<211> LENGTH: 21
<212> TYPE: DNA
<213> ORGANISM: Artificial sequence
<220> FEATURE:
<223> OTHER INFORMATION: Synthetic DNA

<400> SEQUENCE: 33
tgaatcaggg gtgcagactg g                                               21

<210> SEQ ID NO 34
<211> LENGTH: 38
<212> TYPE: DNA
<213> ORGANISM: Artificial sequence
<220> FEATURE:
<223> OTHER INFORMATION: Synthetic DNA

<400> SEQUENCE: 34
acgattgagg cattgcagga tggcggatcg gcgtaacg                             38

<210> SEQ ID NO 35
<211> LENGTH: 39
<212> TYPE: DNA
<213> ORGANISM: Artificial sequence
<220> FEATURE:
<223> OTHER INFORMATION: Synthetic DNA

<400> SEQUENCE: 35
tctgcacccc tgattcacgt gtttctgcgg tgtggtgac                            39

<210> SEQ ID NO 36
<211> LENGTH: 23
<212> TYPE: DNA
<213> ORGANISM: Artificial sequence
<220> FEATURE:
<223> OTHER INFORMATION: Synthetic DNA

<400> SEQUENCE: 36
tgctcatcca ccagataccc gat                                             23

<210> SEQ ID NO 37
<211> LENGTH: 23
<212> TYPE: DNA
<213> ORGANISM: Artificial sequence
<220> FEATURE:
<223> OTHER INFORMATION: Synthetic DNA

<400> SEQUENCE: 37
tctgcactaa gagtcgccgc gtt                                             23
```

<210> SEQ ID NO 38
<211> LENGTH: 26
<212> TYPE: DNA
<213> ORGANISM: Artificial sequence
<220> FEATURE:
<223> OTHER INFORMATION: Synthetic DNA

<400> SEQUENCE: 38
gcttgtgcgt catatagtcg tggaaa                                       26

<210> SEQ ID NO 39
<211> LENGTH: 23
<212> TYPE: DNA
<213> ORGANISM: Artificial sequence
<220> FEATURE:
<223> OTHER INFORMATION: Synthetic DNA

<400> SEQUENCE: 39
ggagggaggc cgaatgcacg atg                                          23

<210> SEQ ID NO 40
<211> LENGTH: 38
<212> TYPE: DNA
<213> ORGANISM: Artificial sequence
<220> FEATURE:
<223> OTHER INFORMATION: Synthetic DNA

<400> SEQUENCE: 40
cgactatatg acgcacaagc tggcggatcg gcgtaacg                          38

<210> SEQ ID NO 41
<211> LENGTH: 42
<212> TYPE: DNA
<213> ORGANISM: Artificial sequence
<220> FEATURE:
<223> OTHER INFORMATION: Synthetic DNA

<400> SEQUENCE: 41
cgtgcattcg gcctccctcc cgtgtttctg cggtgtggtg ac                     42

<210> SEQ ID NO 42
<211> LENGTH: 25
<212> TYPE: DNA
<213> ORGANISM: Artificial sequence
<220> FEATURE:
<223> OTHER INFORMATION: Synthetic DNA

<400> SEQUENCE: 42
caggtccatg ccttcaatca gcgtc                                        25

<210> SEQ ID NO 43
<211> LENGTH: 26
<212> TYPE: DNA
<213> ORGANISM: Artificial sequence
<220> FEATURE:
<223> OTHER INFORMATION: Synthetic DNA

<400> SEQUENCE: 43
gcatgatccc caaggccata cacact                                       26

<210> SEQ ID NO 44
<211> LENGTH: 23
<212> TYPE: DNA
<213> ORGANISM: Artificial sequence
<220> FEATURE:

<223> OTHER INFORMATION: Synthetic DNA

<400> SEQUENCE: 44
aaacgctggc ccgctttcac atg                                    23

<210> SEQ ID NO 45
<211> LENGTH: 25
<212> TYPE: DNA
<213> ORGANISM: Artificial sequence
<220> FEATURE:
<223> OTHER INFORMATION: Synthetic DNA

<400> SEQUENCE: 45
tattgatccg atgcccctga cggtt                                  25

<210> SEQ ID NO 46
<211> LENGTH: 42
<212> TYPE: DNA
<213> ORGANISM: Artificial sequence
<220> FEATURE:
<223> OTHER INFORMATION: Synthetic DNA

<400> SEQUENCE: 46 tcagggcat cggatcaata tggcggatcg gcgtaacgta gc                 42

<210> SEQ ID NO 47
<211> LENGTH: 42
<212> TYPE: DNA
<213> ORGANISM: Artificial sequence
<220> FEATURE:
<223> OTHER INFORMATION: Synthetic DNA

<400> SEQUENCE: 47
gtgaaagcgg gccagcgttt cgtgtttctg cggtgtggtg ac               42

<210> SEQ ID NO 48
<211> LENGTH: 25
<212> TYPE: DNA
<213> ORGANISM: Artificial sequence
<220> FEATURE:
<223> OTHER INFORMATION: Synthetic DNA

<400> SEQUENCE: 48
ctaacaggcg cttacgatga ggtct                                  25

<210> SEQ ID NO 49
<211> LENGTH: 22
<212> TYPE: DNA
<213> ORGANISM: Artificial sequence
<220> FEATURE:
<223> OTHER INFORMATION: Synthetic DNA

<400> SEQUENCE: 49
ctacctgcac aaaacgtccc ga                                     22

<210> SEQ ID NO 50
<211> LENGTH: 23
<212> TYPE: DNA
<213> ORGANISM: Artificial sequence
<220> FEATURE:
<223> OTHER INFORMATION: Synthetic DNA

<400> SEQUENCE: 50
gaggcgacga gacacttcga aga                                    23

```
<210> SEQ ID NO 51
<211> LENGTH: 24
<212> TYPE: DNA
<213> ORGANISM: Artificial sequence
<220> FEATURE:
<223> OTHER INFORMATION: Synthetic DNA

<400> SEQUENCE: 51
tacaagcctc gggtatcgcc attc                                           24

<210> SEQ ID NO 52
<211> LENGTH: 40
<212> TYPE: DNA
<213> ORGANISM: Artificial sequence
<220> FEATURE:
<223> OTHER INFORMATION: Synthetic DNA

<400> SEQUENCE: 52
cgatacccga ggcttgtatg gcggatcggc gtaacgtagc                          40

<210> SEQ ID NO 53
<211> LENGTH: 41
<212> TYPE: DNA
<213> ORGANISM: Artificial sequence
<220> FEATURE:
<223> OTHER INFORMATION: Synthetic DNA

<400> SEQUENCE: 53
tcgaagtgtc tcgtcgcctc cgtgtttctg cggtgtggtg a                        41

<210> SEQ ID NO 54
<211> LENGTH: 24
<212> TYPE: DNA
<213> ORGANISM: Artificial sequence
<220> FEATURE:
<223> OTHER INFORMATION: Synthetic DNA

<400> SEQUENCE: 54
atcatgtcgc ctgcaaatcg ttat                                           24

<210> SEQ ID NO 55
<211> LENGTH: 21
<212> TYPE: DNA
<213> ORGANISM: Artificial sequence
<220> FEATURE:
<223> OTHER INFORMATION: Synthetic DNA

<400> SEQUENCE: 55
agcggcttcg gcacaaagtc c                                              21

<210> SEQ ID NO 56
<211> LENGTH: 23
<212> TYPE: DNA
<213> ORGANISM: Artificial sequence
<220> FEATURE:
<223> OTHER INFORMATION: Synthetic DNA

<400> SEQUENCE: 56
ttggaattgt gggggtggga gat                                            23

<210> SEQ ID NO 57
<211> LENGTH: 25
<212> TYPE: DNA
<213> ORGANISM: Artificial sequence
<220> FEATURE:
<223> OTHER INFORMATION: Synthetic DNA
```

<400> SEQUENCE: 57
cacaaatctc cgggaaaact gccat                                          25

<210> SEQ ID NO 58
<211> LENGTH: 42
<212> TYPE: DNA
<213> ORGANISM: Artificial sequence
<220> FEATURE:
<223> OTHER INFORMATION: Synthetic DNA

<400> SEQUENCE: 58
agttttcccg gagatttgtg tggcggatcg gcgtaacgta gc                       42

<210> SEQ ID NO 59
<211> LENGTH: 41
<212> TYPE: DNA
<213> ORGANISM: Artificial sequence
<220> FEATURE:
<223> OTHER INFORMATION: Synthetic DNA

<400> SEQUENCE: 59 cccacccca caattccaac gtgtttctgc ggtgtggtga c                        41

<210> SEQ ID NO 60
<211> LENGTH: 22
<212> TYPE: DNA
<213> ORGANISM: Artificial sequence
<220> FEATURE:
<223> OTHER INFORMATION: Synthetic DNA

<400> SEQUENCE: 60
gcagcccaac ccagccgatg at                                             22

<210> SEQ ID NO 61
<211> LENGTH: 24
<212> TYPE: DNA
<213> ORGANISM: Artificial sequence
<220> FEATURE:
<223> OTHER INFORMATION: Synthetic DNA

<400> SEQUENCE: 61
cattctttca agggcgcaga ccat                                           24

<210> SEQ ID NO 62
<211> LENGTH: 24
<212> TYPE: DNA
<213> ORGANISM: Artificial sequence
<220> FEATURE:
<223> OTHER INFORMATION: Synthetic DNA

<400> SEQUENCE: 62
ccttcaatat ggtacgcgct cctg                                           24

<210> SEQ ID NO 63
<211> LENGTH: 24
<212> TYPE: DNA
<213> ORGANISM: Artificial sequence
<220> FEATURE:
<223> OTHER INFORMATION: Synthetic DNA

<400> SEQUENCE: 63
agctgtaacc attcaaggct ggcg                                           24

<210> SEQ ID NO 64
<211> LENGTH: 38

```
<212> TYPE: DNA
<213> ORGANISM: Artificial sequence
<220> FEATURE:
<223> OTHER INFORMATION: Synthetic DNA

<400> SEQUENCE: 64
agcgcgtacc atattgaagg tggcggatcg gcgtaacg                              38

<210> SEQ ID NO 65
<211> LENGTH: 42
<212> TYPE: DNA
<213> ORGANISM: Artificial sequence
<220> FEATURE:
<223> OTHER INFORMATION: Synthetic DNA

<400> SEQUENCE: 65
agccttgaat ggttacagct cgtgtttctg cggtgtggtg ac                        42

<210> SEQ ID NO 66
<211> LENGTH: 26
<212> TYPE: DNA
<213> ORGANISM: Artificial sequence
<220> FEATURE:
<223> OTHER INFORMATION: Synthetic DNA

<400> SEQUENCE: 66
ttgtcggaac acacctgaaa acacgg                                          26

<210> SEQ ID NO 67
<211> LENGTH: 26
<212> TYPE: DNA
<213> ORGANISM: Artificial sequence
<220> FEATURE:
<223> OTHER INFORMATION: Synthetic DNA

<400> SEQUENCE: 67
atccaatccg ttacgctccc tacacc                                          26

<210> SEQ ID NO 68
<211> LENGTH: 25
<212> TYPE: DNA
<213> ORGANISM: Artificial sequence
<220> FEATURE:
<223> OTHER INFORMATION: Synthetic DNA

<400> SEQUENCE: 68
atattcaggc ttcaggtttc caggc                                           25

<210> SEQ ID NO 69
<211> LENGTH: 25
<212> TYPE: DNA
<213> ORGANISM: Artificial sequence
<220> FEATURE:
<223> OTHER INFORMATION: Synthetic DNA

<400> SEQUENCE: 69
ggaagcattc tcacgcccta tgacc                                           25

<210> SEQ ID NO 70
<211> LENGTH: 42
<212> TYPE: DNA
<213> ORGANISM: Artificial sequence
<220> FEATURE:
<223> OTHER INFORMATION: Synthetic DNA

<400> SEQUENCE: 70
```
tgaagatcgg ttttctggtc tggcggatcg gcgtaacgta gc                           42

<210> SEQ ID NO 71
<211> LENGTH: 41
<212> TYPE: DNA
<213> ORGANISM: Artificial sequence
<220> FEATURE:
<223> OTHER INFORMATION: Synthetic DNA

<400> SEQUENCE: 71
aaacctgaag cctgaatatc gtgtttctgc ggtgtggtga c                            41

<210> SEQ ID NO 72
<211> LENGTH: 24
<212> TYPE: DNA
<213> ORGANISM: Artificial sequence
<220> FEATURE:
<223> OTHER INFORMATION: Synthetic DNA

<400> SEQUENCE: 72
gccggccatg attgttacgg tact                                              24

<210> SEQ ID NO 73
<211> LENGTH: 24
<212> TYPE: DNA
<213> ORGANISM: Artificial sequence
<220> FEATURE:
<223> OTHER INFORMATION: Synthetic DNA

<400> SEQUENCE: 73
aaacgcattt cccttccgca tcac                                              24

<210> SEQ ID NO 74
<211> LENGTH: 25
<212> TYPE: DNA
<213> ORGANISM: Artificial sequence
<220> FEATURE:
<223> OTHER INFORMATION: Synthetic DNA

<400> SEQUENCE: 74
cctcaaatag aagtctggct cggct                                             25

<210> SEQ ID NO 75
<211> LENGTH: 24
<212> TYPE: DNA
<213> ORGANISM: Artificial sequence
<220> FEATURE:
<223> OTHER INFORMATION: Synthetic DNA

<400> SEQUENCE: 75
tcaattaccg aggctcaaca gggt                                              24

<210> SEQ ID NO 76
<211> LENGTH: 40
<212> TYPE: DNA
<213> ORGANISM: Artificial sequence
<220> FEATURE:
<223> OTHER INFORMATION: Synthetic DNA

<400> SEQUENCE: 76
cagacttcta tttgaggctg gcggatcggc gtaacgtagc                             40

<210> SEQ ID NO 77
<211> LENGTH: 42
<212> TYPE: DNA
<213> ORGANISM: Artificial sequence -continued
<220> FEATURE:
<223> OTHER INFORMATION: Synthetic DNA

<400> SEQUENCE: 77
tgttgagcct cggtaattga cgtgtttctg cggtgtggtg ac                42

METHOD FOR IMPROVING YIELD AND PRODUCTION INTENSITY OF *GLUCONOBACTER OXYDANS* SORBOSE

TECHNICAL FIELD

The disclosure herein relates to a method for improving the yield and production intensity of *Gluconobacter oxydans* (*G. oxydans*) sorbose, and belongs to the technical field of fermentation engineering.

SEQUENCE LISTING STATEMENT

The contents of the electronic sequence listing created on Oct. 15, 2019, named "seq.txt" and 35 KB in size, is hereby incorporated by reference in its entirety.

BACKGROUND

L-sorbose is a ketohexose, which is an important raw material for producing a direct precursor of vitamin C, 2-keto-L-gulonic acid (2-KLG for short). A method for industrially producing sorbose is mainly to ferment D-sorbitol to form L-sorbose by using *G. oxydans*. Sorbose further forms the direct precursor of vitamin C, 2-keto-L-gulonic acid (2-KLG for short), by a "microbial fermentation method" or "Reichstein method". 2-KLG is subjected to lactonization and enolization to obtain Vitamin C. Therefore, the transformation rate of D-sorbitol to L-sorbose determines the transformation rate of vitamin C produced industrially.

*G. oxydans* is a major strain for industrially producing L-sorbose, and sorbitol dehydrogenase on its cell membrane may catalyze D-sorbitol to form L-sorbose. In addition to sorbitol dehydrogenase, the cell membrane of *G. oxydans* also contains a large quantity of other dehydrogenases, such as glucose dehydrogenase. Some of the dehydrogenases have a broad substrate spectrum, which may catalyze D-sorbitol to form other heterosaccharides such as fructose, thereby affecting the transformation rate of D-sorbitol to L-sorbose. A *G. oxydans* genome is modified by a genetic engineering means, and part of a dehydrogenase gene of *G. oxydans* is knocked out, which is expected to solve the problem of accumulation of by-products such as fructose in a fermentation process.

At present, research on the production of L-sorbose by a microbial fermentation method mainly focuses on the optimization and control of the fermentation process of *G. oxydans*, but there are few reports on the molecular modification of the *G. oxydans* genome. Although simple fermentation optimization may reduce the production of by-products to a certain extent, it cannot fundamentally solve the problem of accumulation of by-products in the fermentation process. With the development of a gene sequencing technology, metabolic engineering, synthetic biology and other methods and technologies, the *G. oxydans* genome is modified at a molecular level, which is expected to fundamentally overcome the defects of traditional strains in the fermentation process. At present, the overexpression of sorbitol dehydrogenase by a metabolic engineering method may improve the production intensity of sorbose and shorten a fermentation period, but merely the overexpression of sorbitol dehydrogenase cannot solve the problem that other dehydrogenases catalyze D-sorbitol to form by-products in the fermentation process.

SUMMARY

The present disclosure provides a method for enhancing the production intensity and transformation rate of L-sorbose by fermentation by knocking out dehydrogenase genes forming metabolic by-products thereof.

The present disclosure is firstly directed to a method for improving the yield and production intensity of L-sorbose by modifying a *G. oxydans* genome to knock out genes related to formation of an L-sorbose metabolic by-product.

In an embodiment of the present disclosure, the genes related to formation of the metabolic byproduct include: GDH, GA-5-DH, XDH2, ALDH, XDH, sDH SLC, PTS, PQQ-dependent DH3, NADH-DH, and NADH-dependent ADH genes.

In an embodiment of the present disclosure, the GDH contains a nucleotide sequence shown in SEQ ID NO. 1; the GA-5-DH contains a nucleotide sequence shown in SEQ ID NO. 2; the XDH2 contains a nucleotide sequence shown in SEQ ID NO. 3; the ALDH contains a nucleotide sequence shown in SEQ ID NO. 4; the XDH contains a nucleotide sequence shown in SEQ ID NO. 5; the sDH SLC contains a nucleotide sequence shown in SEQ ID NO. 6; the PTS contains a nucleotide sequence shown in SEQ ID NO. 7; the PQQ-dependent DH3 contains a nucleotide sequence shown in SEQ ID NO. 8; the NADH-DH contains a nucleotide sequence shown in SEQ ID NO. 9; and the NADH-dependent ADH contains a nucleotide sequence shown in SEQ ID NO. 10.

In an embodiment of the present disclosure, the production strain uses *G. oxydans* CGMCC 1.110 as an original strain.

The present disclosure is secondly directed to a recombinant strain for improving the transformation rate and production intensity of L-sorbose. Genes related to formation of major metabolic by-products generated by synthesis of sorbose in a metabolic pathway of L-sorbose produced by the recombinant strain are knocked out. The major metabolic byproducts include, but not limited to, fructose.

In an embodiment of the present disclosure, the genes related to formation of the major metabolic byproducts include: GDH, GA-5-DH, XDH2, ALDH, XDH, sDH SLC, PTS, PQQ-dependent DH3, NADH-DH, and NADH-dependent ADH genes.

In an embodiment of the present disclosure, the recombinant strain uses *G. oxydans* as a host.

In an embodiment of the present disclosure, the recombinant strain uses *G. oxydans* CGMCC 1.110 as a host, and at least one of GDH, GA-5-DH, XDH2, ALDH, XDH, sDH SLC, PTS, PQQ-dependent DH3, NADH-DH, and NADH-dependent ADH genes is knocked out by a homologous recombination method.

The present disclosure is thirdly directed to a method for constructing the recombinant strain. The method includes: respectively amplifying 1000 bp sequences of a target gene in the upstream and downstream of a *G. oxydans* CGMCC 1.110 genome, and fusing with a resistance gene and a negative selective marker gene to construct a knockout box: left homologous arm (HAL)-resistance gene-negative selective marker gene-right homologous arm (HAR); ligating the knockout box to a vector and transforming into a competent cell of *G. oxydans*; carrying out first screening in a resistance marker-containing D-sorbitol medium, and carrying out second screening in a negative selective marker analog-containing D-sorbitol medium.

In an embodiment of the present disclosure, the resistance gene is a gene encoding antibiotic resistance, including but not limited to, kanamycin resistance and ampicillin resistance.

In an embodiment of the present disclosure, the negative selective marker gene is an upp gene, and a negative selective marker analog is 5-fluorouracil.

In an embodiment of the present disclosure, the method specifically includes: respectively amplifying 1000 bp sequences of the target gene in the upstream and downstream of the G. oxydans CGMCC 1.110 genome, and fusing with the kana resistance gene and the upp gene to construct a knockout box: left homologous arm (HAL)-kana-upp-right homologous arm (HAR); ligating the knockout box to a pMD19-T vector; transforming a correctly sequenced knockout box fragment into a competent cell of G. oxydans, carrying out first screening in a kanamycin-containing D-sorbitol medium, and carrying out second screening in a 5-fluorouracil-containing D-sorbitol medium to finally obtain G. oxydans, i.e., G. oxydans-1, G. oxydans-2, G. oxydans-3, G. oxydans-4, G. oxydans-5, G. oxydans-6, G. oxydans-7, G. Oxydans-8, G. oxydans-9, G. oxydans-10 and G. oxydans-11.

In an embodiment of the present disclosure, an upp gene sequence is shown in SEQ ID NO. 11.

The present disclosure is fourthly directed to a method for producing L-sorbose by fermentation using the recombinant strain. The method includes the steps of activating the recombinant strain, inoculating into a fermentation medium, and fermenting and culturing under the conditions of 28 to 30° C. and 200 to 220 rpm.

In an embodiment of the present disclosure, the fermentation medium contains 280 to 350 g of D-sorbitol, 0.4 to 0.6 g of yeast extract, 1.5 to 2.5 g of liquid corn syrup, and 0.5 to 1 g of light calcium carbonate per L.

In an embodiment of the present disclosure, a seed medium contains 180 to 200 g of D-sorbitol, 6 to 8 g of yeast extract, and 2 to 4 g of calcium carbonate per L.

In an embodiment of the present disclosure, the fermentation medium contains 280 to 350 g of D-sorbitol, 0.4 to 0.6 g of yeast extract, 1.5 to 2.5 g of liquid corn syrup, 0.5 to 1 g of light calcium carbonate, and 0.2 g of defoamer per L.

In an embodiment of the present disclosure, a seed liquid is directly inoculated into a conical flask by a glycerin tube to be cultured for 48 h to obtain a first-stage seed, and the $OD_{600}$ of the first-stage seed is about 2 to 3; the first-stage seed is transferred at an inoculation quantity of 1%, and cultured for 24 h to obtain a fermentation seed liquid, having $OD_{600}$ of about 2 to 3; and the fermentation seed liquid is transferred to a fermentor at an inoculation quantity of 25%, and fermented at a temperature of 37° C.

The present disclosure also claims disclosure of the method in preparation of an L-sorbose-containing product.

The beneficial effects are as follows: the methods of the present disclosure may improve the yield and production intensity of L-sorbose; the recombinant strain G. oxydan-11 constructed according to the present disclosure, compared with a control strain G. oxydans CGMCC 1.110, has an L-sorbose transformation rate of 96.12%, which is 4.47% higher than that of the control strain, has a production intensity of 14 g/L·h, which is 14.7% higher than that of a wild strain, and has a fructose by-product content of only 5.6 g/L, which is 45.6% lower than that of the wild strain

DETAILED DESCRIPTION

Determination of sorbitol and sorbose: detection was carried out by high performance liquid chromatography (HPLC). Instrument: Agilent 1260 high performance liquid chromatograph (equipped with an UV-Vis detector and a refractive index detector); chromatographic conditions: Aminex HPX-87H (Bio-Rad), mobile phase: dilute $H_2SO_4$, concentration: 5 mmol·$L^{-1}$, flow rate: 0.5 mL·$min^{-1}$, column temperature: 40° C., and injection volume: 10 µL. (by-products were detected) at 210 nm, and L-sorbose was detected by the refractive index detector; sample preparation: 1 mL of a fermentation broth was centrifuged at 12,000 rpm for 5 min, and a supernatant was appropriately diluted and filtered through a 0.22 µl filter membrane to be subjected to high performance liquid chromatography analysis.

A seed medium (g/L) containing 200 g of D-sorbitol and 10 g of yeast powder was diluted to 1 L in deionized water.

A sorbitol medium for screening, containing 50 g of D-sorbitol and 10 g of yeast powder, was diluted to 1 L in deionized water. A solid medium was added with 2% of agar. (Final concentration of cefoxitin antibiotic: 50 mg/L, final concentration of kana antibiotic: 50 mg/L, and final concentration of 5-fluorouracil: 300 mg/L).

An LB medium containing 10 g of peptone, 5 g of yeast powder, and 10 g of sodium chloride was adjusted to the constant volume of 1 L with deionized water. A solid medium was added with 2% of agar. (Final concentration of ampicillin antibiotic: 100 mg/L).

Production intensity calculation=total mass of L-sorbose in final fermentation broth/(volume of fermentation broth*total fermentation time).

TABLE 1

Primers used for gene knockout

| Primer Name | Primers (5'-3') | Sequence Number |
|---|---|---|
| UPP-F | GACGCCCCTCAGATCGACACGGT | SEQ ID NO. 12 |
| UPP-R | CAGAGCTTTTCGGGCTGCCTGTAC | SEQ ID NO. 13 |
| UPP-CZ-F | ATTCCACCGCCGCCTTCTATGAAAGGAACCTCAGATTTTCTGGAGACTGACCA | SEQ ID NO. 14 |
| UPP-CZ-R | CGAGGAAGCGCCTGAAAACATTGTCTTAACCGGCCATAAAACGGCATGGTAT | SEQ ID NO. 15 |
| Kana-F | TAAACGGACGCACTGGATCTCCTGATGAGGTATTTGGAATGAGTCGCCGTCA | SEQ ID NO. 16 |
| Kana-R | GTCAGTCTCCAGAAAATCTGAGGTTCCTTTCATAGAAGGCGGCGGTGGAA | SEQ ID NO. 17 |
| GDH-F | GCAGCCCAACCCAGCCGATGAT | SEQ ID NO. 18 |

TABLE 1-continued

Primers used for gene knockout

| Primer Name | Primers (5'-3') | Sequence Number |
|---|---|---|
| GDH-R | CATTCTTTCAAGGGCGCAGACCAT | SEQ ID NO. 19 |
| GDH-CZ-F | CCTTCAATATGGTACGCGCTCCTG | SEQ ID NO. 20 |
| GDH-CZ-R | AGCTGTAACCATTCAAGGCTGGCG | SEQ ID NO. 21 |
| GDH-upp-kana-F | AGCGCGTACCATATTGAAGGTGGCGGATCGGCGTAACG | SEQ ID NO. 22 |
| GDH-upp-kana-R | AGCCTTGAATGGTTACAGCTCGTGTTTCTGCGGTGTGGTGAC | SEQ ID NO. 23 |
| GA-5-DH-F | GAAAAGATCCCGGACAGATTGGC | SEQ ID NO. 24 |
| GA-5-DH-R | CGTAGTTGGCCGTCAGGTTGAAAT | SEQ ID NO. 25 |
| GA-5-DH-CZ-F | GGAAGTCGCGCAATGATCATGTCC | SEQ ID NO. 26 |
| GA-5-DH-CZ-R | AGAATTTCAGCCGTCATAGTGGTG | SEQ ID NO. 27 |
| GA-5-DH-upp-kana-F | ATGATCATTGCGCGACTTCCTGGCGGATCGGCGTAACG | SEQ ID NO. 28 |
| GA-5-DH-upp-kana-R | ACTATGACGGCTGAAATTCTCGTGTTTCTGCGGTGTGGTGAC | SEQ ID NO. 29 |
| XDH2-F | AGTCACCTGATCTGGATTGGCG | SEQ ID NO. 30 |
| XDH2-R | TTCCATGCAAGAGAAGGGGACC | SEQ ID NO. 31 |
| XDH2-CZ-F | TCCTGCAATGCCTCAATCGTTC | SEQ ID NO. 32 |
| XDH2-CZ-R | TGAATCAGGGGTGCAGACTGG | SEQ ID NO. 33 |
| XDH2-upp-kana-F | ACGATTGAGGCATTGCAGGATGGCGGATCGGCGTAACG | SEQ ID NO. 34 |
| XDH2-upp-kana-R | TCTGCACCCCTGATTCACGTGTTTCTGCGGTGTGGTGAC | SEQ ID NO. 35 |
| ALDH-F | TGCTCATCCACCAGATACCCGAT | SEQ ID NO. 36 |
| ALDH-R | TCTGCACTAAGAGTCGCCGCGTT | SEQ ID NO. 37 |
| ALDH-CZ-F | GCTTGTGCGTCATATAGTCGTGGAAA | SEQ ID NO. 38 |
| ALDH-CZ-R | GGAGGGAGGCCGAATGCACGATG | SEQ ID NO. 39 |
| ALDH-upp-kana-F | CGACTATATGACGCACAAGCTGGCGGATCGGCGTAACG | SEQ ID NO. 40 |
| ALDH-upp-kana-R | CGTGCATTCGGCCTCCCTCCCGTGTTTCTGCGGTGTGGTGAC | SEQ ID NO. 41 |
| XDH-F | CAGGTCCATGCCTTCAATCAGCGTC | SEQ ID NO. 42 |
| XDH-R | GCATGATCCCCAAGGCCATACACACT | SEQ ID NO. 43 |
| XDH-CZ-R | AAACGCTGGCCCGCTTTCACATG | SEQ ID NO. 44 |
| XDH-CZ-F | TATTGATCCGATGCCCCTGACGGTT | SEQ ID NO. 45 |
| XDH-upp-kana-F | TCAGGGGCATCGGATCAATATGGCGGATCGGCGTAACGTAGC | SEQ ID NO. 46 |
| XDH-upp-kana-R | GTGAAAGCGGGCCAGCGTTTCGTGTTTCTGCGGTGTGGTGAC | SEQ ID NO. 47 |
| sDH SLC-F | CTAACAGGCGCTTACGATGAGGTCT | SEQ ID NO. 48 |
| sDH SLC-R | CTACCTGCACAAAACGTCCCGA | SEQ ID NO. 49 |
| sDH SLC-CZ-F | GAGGCGACGAGACACTTCGAAGA | SEQ ID NO. 50 |

TABLE 1-continued

Primers used for gene knockout

| Primer Name | Primers (5'-3') | Sequence Number |
|---|---|---|
| sDH SLC-CZ-R | TACAAGCCTCGGGTATCGCCATTC | SEQ ID NO. 51 |
| sDH SLC-upp-kana-F | CGATACCCGAGGCTTGTATGGCGGATCGGCGTAACGTAGC | SEQ ID NO. 52 |
| sDH SLC-upp-kana-R | TCGAAGTGTCTCGTCGCCTCCGTGTTTCTGCGGTGTGGTGA | SEQ ID NO. 53 |
| PTS-F | ATCATGTCGCCTGCAAATCGTTAT | SEQ ID NO. 54 |
| PTS-R | AGCGGCTTCGGCACAAAGTCC | SEQ ID NO. 55 |
| PTS-CZ-F | TTGGAATTGTGGGGGTGGGAGAT | SEQ ID NO. 56 |
| PTS-CZ-R | CACAAATCTCCGGGAAAACTGCCAT | SEQ ID NO. 57 |
| PTS-upp-kana-F | AGTTTTCCCGGAGATTTGTGTGGCGGATCGGCGTAACGTAGC | SEQ ID NO. 58 |
| PTS-upp-kana-R | CCCACCCCCACAATTCCAACGTGTTTCTGCGGTGTGGTGAC | SEQ ID NO. 59 |
| PQQ-dependent DH3-F | GCAGCCCAACCCAGCCGATGAT | SEQ ID NO. 60 |
| PQQ-dependent DH3-R | CATTCTTTCAAGGGCGCAGACCAT | SEQ ID NO. 61 |
| PQQ-dependent DH3-CZ-F | CCTTCAATATGGTACGCGCTCCTG | SEQ ID NO. 62 |
| PQQ-dependent DH3-CZ-R | AGCTGTAACCATTCAAGGCTGGCG | SEQ ID NO. 63 |
| PQQ-dependent DH3-upp-kana-F | AGCGCGTACCATATTGAAGGTGGCGGATCGGCGTAACG | SEQ ID NO. 64 |
| PQQ-dependent DH3-upp-kana-R | AGCCTTGAATGGTTACAGCTCGTGTTTCTGCGGTGTGGTGAC | SEQ ID NO. 65 |
| NADH-DH-F | TTGTCGGAACACACCTGAAAACACGG | SEQ ID NO. 66 |
| NADH-DH-R | ATCCAATCCGTTACGCTCCCTACACC | SEQ ID NO. 67 |
| NADH-DH-CZ-R | ATATTCAGGCTTCAGGTTTCCAGGC | SEQ ID NO. 68 |
| NADH-DH-CX-R | GGAAGCATTCTCACGCCCTATGACC | SEQ ID NO. 69 |
| NADH-DH-upp-kana-F | TGAAGATCGGTTTTCTGGTCTGGCGGATCGGCGTAACGTAGC | SEQ ID NO. 70 |
| NADH-DH-upp-kana-R | AAACCTGAAGCCTGAATATCGTGTTTCTGCGGTGTGGTGAC | SEQ ID NO. 71 |
| NADH-dependent ADH-F | GCCGGCCATGATTGTTACGGTACT | SEQ ID NO. 72 |
| NADH-dependent ADH-R | AAACGCATTTCCCTTCCGCATCAC | SEQ ID NO. 73 |
| NADH-dependent ADH-CZ-F | CCTCAAATAGAAGTCTGGCTCGGCT | SEQ ID NO. 74 |
| NADH-dependent ADH-CZ-R | TCAATTACCGAGGCTCAACAGGGT | SEQ ID NO. 75 |
| NADH-dependent ADH-upp-kana-F | CAGACTTCTATTTGAGGCTGGCGGATCGGCGTAACGTAGC | SEQ ID NO. 76 |
| NADH-dependent ADH-upp-kana-R | TGTTGAGCCTCGGTAATTGACGTGTTTCTGCGGTGTGGTGAC | SEQ ID NO. 77 |

Example 1: Construction of Knockout Box of Genes

Primers UPP-F and UPP-R were subjected to PCR to obtain an upp gene fragment using a *G. oxydans* CGMCC 1.110 genome as a template; primers kana-F and Kana-R were subjected to PCR to obtain a kana gene fragment using pBBR1MCS-2 as a template; an upp gene was amplified by primers using the *G. oxydans* CGMCC 1.110 genome as a template, 1000 bp sequences in the upstream and downstream of the gene to be knocked out were amplified by using the *G. oxydans* CGMCC 1.110 genome as a template, and the above four fragments were ligated by fusion PCR to construct a gene knockout box: left homologous arm (HAL)-kana-upp-right homologous arm (HAR), and the knockout box was ligated to a pMD-19-T vector, and transformed into a competent cell JM109 of *Escherichia coli*, transformants were coated on an ampicillin (100 mg/L)-containing LB plate to be screened and sequenced, and a correctly sequenced strain was preserved.

Example 2: Construction of Recombinant Strain *G. oxydans*-1

A knockout box: GDHL-kana-upp-GDHR for knocking out a GDH gene was constructed according to the method of Example 1, including the following specific steps: utilizing primers GDH-F and GDH-CZ-R to obtain a 1000 bp fragment GDHL of a left arm of the GDH gene by PCR using the *G. oxydans* CGMCC 1.110 genome as a template; utilizing primers GDH-R and GDH-CZ-F to obtain a 1000 bp fragment GDHR of a right arm of the GDH gene by PCR using the *G. oxydans* CGMCC 1.110 genome as a template, utilizing primers GDH-upp-kana-F and GDH-upp-kana-R to obtain an upp-kana gene fragment GDH-upp-kana by PCR using the kana-upp constructed in Example 1 as a template, and performing a fusion PCR method on GDH-upp-kana, GDHL and GDHR to obtain GDHL-kana-upp-GDHR. Since the constructed dehydrogenase knockout box carried the kana (the gene sequence was shown in Genbank accession number: MH539767.1)-upp gene, the correctly sequenced dehydrogenase knockout box fragment was transformed into a *G. oxydans* recipient CGMCC 1.110 to obtain an upp gene-defected strain *G. oxydans* (knockout gene: kana-upp), which normally grows in a kanamycin and cefoxitin-containing D-sorbitol medium; and after a first round of screening by kana antibiotics, a second round of screening was performed in a 5-fluorouracil (300 mg/L) and cefoxitin (50 mg/L)-containing D-sorbitol medium to obtain a recombinant strain *G. oxydans*-1 in which the GDH gene was knocked out.

Example 3: Construction of Recombinant Strain *G. oxydans*-2

A knockout box: GA-5-DHL-kana-upp-GA-5-DHR for knocking out a GA-5-DHR gene was constructed according to the method of Example 1, including the following steps: utilizing primers GA-5-DH-F and GA-5-DH-CZ-R to obtain a 1000 bp fragment GA-5-DHL of a left arm of the GA-5-DH gene by PCR using the *G. oxydans* CGMCC 1.110 genome as a template; utilizing primers GA-5-DH-F and GA-5-DH-CZ-R to obtain a 1000 bp fragment GA-5-DHR of a right arm of the GA-5-DH gene by PCR using the *G. oxydans* CGMCC 1.110 genome as a template, utilizing primers GA-5-DH-upp-kana-F and GA-5-DH-upp-kana-R to obtain a GA-5-DH-upp-kana gene fragment by PCR using the kana-upp constructed in Example 1 as a template, and performing a fusion PCR method on GA-5-DH-upp-kana, GA-5-DHL and GA-5-DHR to obtain GA-5-DHL-kana-upp-GA-5-DHR. The correctly sequenced dehydrogenase knockout box fragment was transformed into *G. oxydans* CGMCC 1.110 to obtain a recombinant strain *G. oxydans*-02 in which the GA-5-DH gene was knocked out after screening according to the same method above.

Example 4: Construction of Recombinant Strain *G. oxydans*-3

A knockout box XDH2L-kana-upp-NAD-XDH2R for knocking out an XDH2 gene was constructed according to the method of Example 1, including the following steps: utilizing primers XDH2-F and XDH2-CZ-R to obtain a 1000 bp fragment XDH2L of a left arm of the XDH2 gene by PCR using the *G. oxydans* CGMCC 1.110 genome as a template; utilizing primers XDH2-R and XDH2-CZ-F to obtain a 1000 bp fragment XDHR2 of a right arm of the XDH2 gene by PCR using the *G. oxydans* CGMCC 1.110 genome as a template, utilizing primers XDH2-upp-kana-F and XDH2-upp-kana-R to obtain an XDH2-upp-kana gene fragment by PCR using the kana-upp constructed in Example 1 as a template, and performing a fusion PCR method on XDH2-kana-upp, XDH2L and XDH2R to obtain XDH2L-kana-upp-XDH2R. The correctly sequenced dehydrogenase knockout box fragment was transformed into *G. oxydans* CGMCC 1.110 to obtain a recombinant strain *G. oxydans*-03 in which the XDH2 gene was knocked out after screening according to the above same method.

Example 5: Construction of Recombinant Strain *G. oxydans*-4

A knockout box ALDHL-kana-upp-ALDHR for knocking out an ALDH gene was constructed according to the method of Example 1, including the following steps: utilizing primers ALDH-F and ALDH-CZ-R to obtain a 1000 bp fragment ALDHL of a left arm of the ALDH gene by PCR using the *G. oxydans* CGMCC 1.110 genome as a template; utilizing primers ALDH-R and ALDH-CZ-F to obtain a 1000 bp fragment ALDHR of a right arm of the ALDH gene by PCR using the *G. oxydans* CGMCC 1.110 genome as a template, utilizing primers ALDH-upp-kana-F and ALDH-upp-kana-R to obtain an ALDH-upp-kana gene fragment by PCR using the kana-upp constructed in Example 1 as a template, and performing a fusion PCR method on ALDH-kana-upp, ALDHL and ALDHR to obtain ALDHL-kana-upp-ALDHR. The correctly sequenced dehydrogenase knockout box fragment was transformed into *G. oxydans* CGMCC 1.110 to obtain a recombinant strain *G. oxydans*-04 in which the ALDH gene was knocked out after screening according to the same method above.

Example 6: Construction of Recombinant Strain *G. oxydans*-5

A knockout box XDHL-kana-upp-XDHR for knocking out an XDH gene was constructed according to the method of Example 1, including the following steps: utilizing primers XDH-F and XDH-CZ-R to obtain a 1000 bp fragment XDHL of a left arm of the XDH gene by PCR using the *G. oxydans* CGMCC 1.110 genome as a template; utilizing primers XDH-R and XDH-CZ-F to obtain a 1000 bp fragment XDHR of a right arm of the XDH gene by PCR using the *G. oxydans* CGMCC 1.110 genome as a template, utilizing primers XDH-upp-kana-F and XDH-upp-kana-R to obtain an XDH-upp-kana gene fragment by PCR using the kana-upp constructed in Example 1 as a template, and performing a fusion PCR method on XDH-kana-upp, XDHL and XDHR to obtain XDHL-kana-upp-XDHR. The correctly sequenced dehydrogenase knockout box fragment was transformed into *G. oxydans* CGMCC 1.110 to obtain a recombinant strain *G. oxydans*-05 in which the XDH gene was knocked out after screening according to the same method above.

Example 7: Construction of Recombinant Strain *G. oxydans*-6

A knockout box sDH SLCL-kana-upp-sDH SLCR for knocking out an sDH SLC gene was constructed according to the method of Example 1, including the following steps: utilizing primers SLC-F and SLC-CZ-R to obtain a 1000 bp fragment sDH SLCL of a left arm of the sDH SLC gene by PCR using the *G. oxydans* CGMCC 1.110 genome as a template; utilizing primers SLC-R and SLC-CZ-F to obtain a 1000 bp fragment SLC-R of a right arm of the sDH SLC gene by PCR using the *G. oxydans* CGMCC 1.110 genome as a template, utilizing primers sDH SLC-upp-kana-F and sDH SLC-upp-kana-R to obtain an sDH SLC-upp-kana gene fragment by PCR using the kana-upp constructed in Example 1 as a template, and performing a fusion PCR method on sDH SLC-kana-upp, sDH SLCL and sDH SLCR to obtain sDH SLCL-kana-upp-sDH SLCR. The correctly sequenced dehydrogenase knockout box fragment was transformed into *G. oxydans* CGMCC 1.110 to obtain a recombinant strain *G. oxydans*-06 in which the sDH SLC gene was knocked out after screening according to the same method above.

Example 8: Construction of Recombinant Strain *G. oxydans*-7

A knockout box: PTSL-kana-upp-PTSR for knocking out a PTS gene was constructed according to the method of Example 1, including the following steps: utilizing primers PTS-F and PTS-CZ-R to obtain a 1000 bp fragment PTSL of a left arm of the PTS gene by PCR using the *G. oxydans* CGMCC 1.110 genome as a template; utilizing primers PTS-R and PTS-CZ-F to obtain a 1000 bp fragment PTSR of a right arm of the PTS gene by PCR using the *G. oxydans* CGMCC 1.110 genome as a template, utilizing primers PTS-upp-kana-F and PTS-upp-kana-R to obtain a PTS-upp-kana gene fragment by PCR using the kana-upp constructed in Example 1 as a template, and performing a fusion PCR method on PTS-kana-upp, PTSL and PTSR to obtain PTSL-kana-upp-PTSR. The correctly sequenced dehydrogenase knockout box fragment was transformed into *G. oxydans* CGMCC 1.110 to obtain a recombinant strain *G. oxydans*-07 in which the PTS gene was knocked out after screening according to the same method above.

Example 9: Construction of Recombinant Strain *G. oxydans*-8

A knockout box PQQ-dependent DH3L-kana-upp-PQQ-dependent DH3R for knocking out a PQQ-dependent DH3 gene was constructed according to the method of Example 1, including the following steps: utilizing primers PQQ-dependent DH3-F and PQQ-dependent DH3-CZ-R to obtain a 1000 bp fragment PQQ-dependent DH3L of a left arm of a PQQ-dependent DH3 gene by PCR using the *G. oxydans* CGMCC 1.110 genome as a template; utilizing primers PQQ-dependent DH3-R and PQQ-dependent DH3-CZ-F to obtain a 1000 bp fragment PQQ-dependent DH3R of a right arm of the PQQ-dependent DH3 gene by PCR using the *G. oxydans* CGMCC 1.110 genome as a template, utilizing primers PQQ-dependent DH3-upp-kana-F and PQQ-dependent DH-upp-kana-R to obtain a PQQ-dependent DH3-upp-kana gene fragment by PCR using the kana-upp constructed in Example 1 as a template, and performing a fusion PCR method on PQQ-dependent DH3-kana-upp, PQQ-dependent DH3L and PQQ-dependent DH3R to obtain PQQ-dependent DH3L-kana-upp-PQQ-dependent DH3R. The correctly sequenced dehydrogenase knockout box fragment was transformed into *G. oxydans* CGMCC 1.110 to obtain a recombinant strain *G. oxydans*-08 in which the PQQ-dependent DH3 gene was knocked out after screening according to the same method above.

Example 10: Construction of Recombinant Strain *G. oxydans*-9

A knockout box NADH-DHL-kana-upp-NADH-DHR for knocking out an NADH-DH gene was constructed according to the method of Example 1, including the following steps: utilizing primers NADH-DH-F and NADH-DH-CZ-R to obtain a 1000 bp fragment NADH-DHL of a left arm of the NADH-DH gene by PCR using the *G. oxydans* CGMCC 1.110 genome as a template; utilizing primers NADH-DH-R and NADH-DH-CZ-F to obtain a 1000 bp fragment NADH-DHR of a right arm of the NADH-DH gene by PCR using the *G. oxydans* CGMCC 1.110 genome as a template, utilizing primers NADH-DH-upp-kana-F and NADH-DH-upp-kana-R to obtain an NADH-DH-upp-kana gene fragment by PCR using the kana-upp constructed in Example 1 as a template, and performing a fusion PCR method on NADH-DH-kana-upp, NADH-DHL and NADH-DHR to obtain NADH-DHL-kana-upp-NADH-DHR. The correctly sequenced dehydrogenase knockout box fragment was transformed into *G. oxydans* CGMCC 1.110 to obtain a recombinant strain *G. oxydans*-09 in which the NADH-DH gene was knocked out after screening according to the same method above.

Example 11: Construction of Recombinant Strain *G. oxydans*-10

A knockout box NADH-dependent ADHL-kana-upp-NADH-dependent ADHR for knocking out an NADH-dependent ADH gene was constructed according to the method of Example 1, including the following steps: utilizing primers NADH-dependent ADH-F and NADH-dependent ADH-CZ-R to obtain a 1000 bp fragment NADH-dependent ADHL of a left arm of the NADH-dependent ADH gene by PCR using the *G. oxydans* CGMCC 1.110 genome as a template; utilizing primers NADH-dependent ADH-R and NADH-dependent ADH-CZ-F to obtain a 1000 bp fragment NADH-dependent ADHR of a right arm of the NADH-dependent ADH gene by PCR using the *G. oxydans* CGMCC 1.110 genome as a template, utilizing primers NADH-dependent ADH-upp-kana-F and NADH-dependent ADH-upp-kana-R to obtain an NADH-dependent ADH-upp-kana gene fragment by PCR using the kana-upp constructed in Example 1 as a template, and performing a fusion PCR method on NADH-dependent ADH-kana-upp, NADH-dependent ADHL and NADH-dependent ADHR to obtain NADH-dependent ADHL-kana-upp-NADH-dependent ADHR. The correctly sequenced dehydrogenase knockout box fragment was transformed into *G. oxydans* CGMCC 1.110 to obtain a recombinant strain *G. oxydans*-10 in which the NADH-dependent ADH gene was knocked out after screening according to the same method above.

Example 12: Construction of Recombinant Strain *G. oxydans*-11

(1) A knockout box: GDHL-kana-upp-GDHR for knocking out the GDH gene was constructed according to the method of Example 2 (utilizing primers GDH-F and GDH-CZ-R to obtain a 1000 bp fragment GDHL of a left arm of the GDH gene by PCR using the *G. oxydans* CGMCC 1.110 genome as a template; utilizing primers GDH-R and GDH-CZ-F to obtain a 1000 bp fragment GDHR of a right arm of the GDH gene by PCR using the *G. oxydans* CGMCC 1.110 genome as a template, utilizing primers GDH-upp-kana-F and GDH-upp-kana-R to obtain an upp-kana gene fragment GDH-upp-kana by PCR using the kana-upp constructed in Example 1 as a template, and performing a fusion PCR method on GDH-upp-kana, GDHL and GDHR to obtain GDHL-kana-upp-GDHR). Since the dehydrogenase knockout box carried the kana (Genbank accession number: MH539767.1)-upp gene, the correctly sequenced dehydrogenase knockout box fragment was transformed into the *G. oxydans* recipient CGMCC 1.110 to obtain an upp gene-defected strain *G. oxydans* (knockout gene: kana-upp), which normally grows in a kanamycin and cefoxitin-containing D-sorbitol medium; after a first round of screening by kana antibiotics, a second round of screening was performed in the 5-fluorouracil (300 mg/L) and cefoxitin (50 mg/L)-containing D-sorbitol medium to obtain the recombinant strain *G. oxydans* in which the GDH gene was knocked out;

(2) according to the steps in Example 3, the constructed knockout box GA-5-DHL-kana-upp-GA-5-DHR was transformed into the *G. oxydans* recombinant strain constructed in step (1), and a recombinant strain in which the GDH and GA-5-DH genes were knocked out was obtained after screening according to the same method as in step (1);

(3) according to the steps in Example 4, the constructed knockout box XDH2L-kana-upp-NAD-XDH2R was transformed into the *G. oxydans* recombinant strain constructed in step (2), and a recombinant strain in which the GDH, GA-5-DHXDH2 and XDH2 genes were knocked out was obtained after screening according to the same method as above;

(4) according to the steps in Example 5, the constructed knockout box ALDHL-kana-upp-ALDHR was transformed into the *G. oxydans* recombinant strain constructed in step (3), and a recombinant strain in which the GDH, GA-5-DHXDH, XDH2 and ALDH genes were knocked out was obtained after screening according to the same method as above;

(5) according to the steps in Example 6, the constructed knockout box XDHL-kana-upp-XDHR was transformed into the *G. oxydans* recombinant strain constructed in step (4), and a recombinant strain in which the GDH, GA-5-DHXDH, XDH2, ALDH and XDH genes were knocked out was obtained after screening according to the same method as above;

(6) according to the steps in Example 7, the constructed knockout box sDH SLCL-kana-upp-sDH SLCR was transformed into the *G. oxydans* recombinant strain constructed in step (5), and a recombinant strain in which the GDH, GA-5-DHXDH, XDH2, ALDH, XDH and sDH SLC genes were knocked out was obtained after screening according to the same method as above;

(7) according to the steps in Example 8, the constructed knockout box sDH PTSL-kana-upp-PTSR was transformed into the *G. oxydans* recombinant strain constructed in step (6), and a recombinant strain in which the GDH, GA-5-DHXDH, XDH2, ALDH, XDH, sDH SLC and PTS genes were knocked out was obtained after screening according to the same method as above;

(8) according to the steps in Example 9, the constructed knockout box PQQ-dependent DH3 was transformed into the *G. oxydans* recombinant strain constructed in step (7), and a recombinant strain in which the GDH, GA-5-DHXDH, XDH2, ALDH, XDH, sDH SLC, PTS and PQQ-dependent DH3 genes were knocked out was obtained after screening according to the same method as above;

(9) according to the steps in Example 10, the constructed knockout box NADH-DH was transformed into the *G. oxydans* recombinant strain constructed in step (8), and a recombinant strain in which the GDH, GA-5-DHXDH, XDH2, ALDH, XDH, sDH SLC, PTS, PQQ-dependent DH3 and NADH-DH genes were knocked out was obtained after screening according to the same method as above; and

(10) according to the steps in Example 11, the constructed knockout box NADH-DH was transformed into the *G. oxydans* recombinant strain constructed in step (9), and a recombinant strain *G. oxydans*-11 (*G. oxydans* CGMCC 1.110 (AGDH, GA-5-DH, XDH2, ALDH, XDH, sDH SLC, PTS, PQQ-dependent DH3, NADH-DH, NADH-dependent ADH) in which the GDH, GA-5-DH, XDH2, ALDH, XDH, sDH SLC, PTS, PQQ-dependent DH3, NADH-DH and NADH-dependent ADH genes were knocked out was obtained after screening according to the same method above.

Example 13: Production of Sorbose by Fermentation Using Recombinant Strain and Control Strain The recombinant strain *G. oxydans*-10 prepared in Example 11 and a control strain *G. oxydans* CGMCC 1.110 were selected and respectively activated and cultured on a seed medium for 24 to 36 h, and the above-mentioned activated and cultured seed liquids were respectively inoculated into a fermentation medium (containing, by g/L, 280 to 350 g of D-sorbitol, 0.4 to 0.6 g of yeast extract, 1.5 to 2.5 g of liquid corn syrup, and 0.5 to 1 g of light calcium carbonate) at an inoculation quantity of 25% to be fermented and cultured under the conditions of 37° C. and 750 rpm, and fermented for 15 to 20 h, and dissolved oxygen and pH in the fermentation process were detected; and after the fermentation dissolved oxygen began to rise for 2.5 h, the fermentation was terminated, and the fermentation broth L-sorbose and fructose contents were detected. The fermentation results are shown in Table 1. Compared with the control strain *G. oxydans* CGMCC 1.110, the transformation rate of *G. oxydans*-11 was increased to 96.12%, the production intensity was increased by 14.7%, and the fructose by-product was decreased by 45.6%.

TABLE 2

Fermentation results of G. oxydans from which different dehydrogenases are knocked out

| | Sorbose content | Transformation rate | Fructose content |
|---|---|---|---|
| G. oxydans CGMCC 1.110 | 265.8 g/L | 91.65% | 10.3 g/L |
| G. oxydans-1 | 267.8 g/L | 92.83% | 9.2 g/L |
| G. oxydans-2 | 269.1 g/L | 93.27% | 8.6 g/L |
| G. oxydans-3 | 269.4 g/L | 93.38% | 8.2 g/L |
| G. oxydans-4 | 267.2 g/L | 92.62% | 9.6 g/L |
| G. oxydans-5 | 270.8 g/L | 93.87% | 7.5 g/L |
| G. oxydans-6 | 273.4 g/L | 94.77% | 6.7 g/L |
| G. oxydans-7 | 269.7 g/L | 93.52% | 9.1 g/L |
| G. oxydans-8 | 269.3 g/L | 93.35% | 9.4 g/L |
| G. oxydans-9 | 268.8 g/L | 93.17% | 8.3 g/L |
| G. oxydans-10 | 272.2 g/L | 94.35% | 6.9 g/L |
| G. oxydans-11 | 277.3 g/L | 96.12% | 5.6 g/L |

Example 14: Disclosure of Gene Knockout in Improvement on Sorbose Transformation Rate in Other G. oxydans The knockout method was applied to other G. oxydans according to the methods of Examples 1 and 2, which specifically includes: knocking out the PQQ-dependent DH3 gene of G. oxydans 621H; knocking out the gDH gene of G. oxydans CGMCC 1.049; and knocking out the Sdh-SLC gene of G. oxydans WSH-003. G. oxydans 621H was purchased from ATCC, and G. oxydans CGMCC 1.049 was purchased from CGMCC. G. oxydans WSH-003 was disclosed in the patent with the publication number of CN 104611285 B. The recombinant strain was fermented in the same manner as in Example 12.

The results are shown in Table 2. The method of the present disclosure may still improve the transformation efficiency of D-sorbitol to L-sorbose by G. oxydans to varying degrees, indicating that the method may be applied to most G. oxydans.

TABLE 3

Fermentation results of different G. oxydans from which different dehydrogenases are knocked out

| Strains/(knockout genes) | | L-sorbose yield | Transformation rate | Fructose content |
|---|---|---|---|---|
| G. oxydans 621H (PQQ-dependent DH3 (Genbank accession number: GOX1441)) | Before knockout | 260.7 g/L | 90.37% | 12.3 g/L |
| | After knockout | 263.4 g/L | 91.30% | 9.6 g/L |
| G. oxydans CGMCC 1.049 (gDH) | Before knockout | 258.7 g/L | 89.67% | 14.5 g/L |
| | After knockout | 262.8 g/L | 91.09% | 10.7 g/L |
| G. oxydans WSH-003 (sDH-SLC) | Before knockout | 265.4 g/L | 92.00% | 11.3 g/L |
| | After knockout | 268.7 g/L | 93.14% | 8.9 g/L |

What is claimed is:

1. A method for improving yield and production intensity of L-sorbose in *Gluconobacter oxydans*, comprising knocking out genes related to formation of an L-sorbose metabolic byproduct, wherein the genes related to formation of the L-sorbose metabolic byproduct comprise at least one of GDH, GA-5-DH, XDH2, ALDH, XDH, sDH SLC, PTS, PQQ-dependent DH3, NADH-DH, and NADH-dependent ADH genes; and the GDH contains the nucleotide sequence set forth in SEQ ID NO: 1; the GA-5-DH contains the nucleotide sequence set forth in SEQ ID NO: 2; the XDH2 contains the nucleotide sequence set forth in SEQ ID NO: 3; the ALDH contains the nucleotide sequence set forth in SEQ ID NO: 4; the XDH contains the nucleotide sequence set forth in SEQ ID NO: 5; the sDH SLC contains the nucleotide sequence set forth in SEQ ID NO: 6; the PTS contains the nucleotide sequence set forth in SEQ ID NO: 7; the PQQ-dependent DH3 contains the nucleotide sequence set forth in SEQ ID NO: 8; the NADH-DH contains the nucleotide sequence set forth in SEQ ID NO: 9; and the NADH-dependent ADH contains the nucleotide sequence set forth in SEQ ID NO: 10.

2. The method according to claim 1, wherein the following genes are knocked out: (a) the GDH gene set forth in SEQ ID NO: 1; (b) the GA-5-DH gene set forth in SEQ ID NO: 2; (c) the XDH2 gene set forth in SEQ ID NO: 3; (d) the ALDH gene set forth in SEQ ID NO: 4; (e) the XDH gene set forth in SEQ ID NO: 5; (f) the sDH SLC gene set forth in SEQ ID NO: 6; (g) the PTS gene set forth in SEQ ID NO: 7; (h) the PQQ-dependent DH3 gene set forth in SEQ ID NO: 8; (i) the NADH-DH gene set forth in SEQ ID NO: 9; (j) the NADH-dependent ADH gene set forth in SEQ ID NO: 10; and (k) a combination of the genes of (a) to (j).

3. A genetically engineered *Gluconobacter oxydans* strain for producing L-sorbose, wherein genes related to formation of major metabolic byproducts generated by synthesis of sorbose in a metabolic pathway of L-sorbose production are knocked out; the major metabolic byproducts comprise fructose; and the genes related to formation of the L-sorbose metabolic byproducts comprise at least one of GDH, GA-5-DH, XDH2, ALDH, XDH, sDH SLC, PTS, PQQ-dependent DH3, NADH-DH, and NADH-dependent ADH genes; and the GDH contains the nucleotide sequence set forth in SEQ ID NO: 1; the GA-5-DH contains the nucleotide sequence set forth in SEQ ID NO: 2; the XDH2 contains the nucleotide sequence set forth in SEQ ID NO: 3; the ALDH contains the nucleotide sequence set forth in SEQ ID NO: 4; the XDH contains the nucleotide sequence set forth in SEQ ID NO: 5; the sDH SLC contains the nucleotide sequence set forth in SEQ ID NO: 6; the PTS contains the nucleotide sequence set forth in SEQ ID NO: 7; the PQQ-dependent DH3 contains the nucleotide sequence set forth in SEQ ID NO: 8; the NADH-DH contains the nucleotide sequence set forth in SEQ ID NO: 9; and the NADH-dependent ADH contains the nucleotide sequence set forth in SEQ ID NO: 10.

4. The genetically engineered strain according to claim 3, wherein the following genes are knocked out: (a) the GDH gene set forth in SEQ ID NO: 1; (b) the GA-5-DH gene set forth in SEQ ID NO: 2; (c) the XDH2 gene set forth in SEQ ID NO: 3; (d) the ALDH gene set forth in SEQ ID NO: 4; (e) the XDH gene set forth in SEQ ID NO: 5; (f) the sDH SLC gene set forth in SEQ ID NO: 6; (g) the PTS gene set forth in SEQ ID NO: 7; (h) the PQQ-dependent DH3 gene set forth in SEQ ID NO: 8; (i) the NADH-DH gene set forth in SEQ ID NO: 9; (j) the NADH-dependent ADH gene set forth in SEQ ID NO: 10; and (k) a combination of the genes of (a) to (j).

5. A method for constructing the genetically engineered strain according to claim 4, comprising: separately amplifying 800 to 1200 bp sequences of a target gene in the upstream and downstream of a genome, and fusing with a resistance gene and a negative selective marker gene to construct a knockout box: left homologous arm (HAL)-resistance gene-negative selective marker gene-right homologous arm (HAR); ligating the knockout box to a vector, and transforming into a competent cell of a host; carrying out first screening in a resistance marker-containing medium; and carrying out second screening in a negative selective marker analog-containing medium.

6. The method according to claim 5, wherein the resistance gene is a gene encoding antibiotic resistance, the negative selective marker gene is an upp gene, and a negative selective marker analog is 5-fluorouracil.

7. A method for producing L-sorbose, comprising: inoculating the genetically engineered strain according to claim 4 to a fermentation medium; and fermenting and culturing under conditions of 28 to 30° C. and 200 to 220 rpm.

8. The method according to claim 7, wherein the fermentation medium contains 280 to 350 g of D-sorbitol, 0.4 to 0.6 g of yeast extract, 1.5 to 2.5 g of liquid corn syrup, and 0.5 to 1 g of light calcium carbonate per L.

9. The method according to claim 7, further comprising carrying out seed culture of the genetically engineered strain, wherein a seed medium for seed culture contains 180 to 200 g of D-sorbitol, 6 to 8 g of yeast extract, and 2 to 4 g of calcium carbonate per L.

10. The method according to claim 7, further comprising: inoculating the genetically engineered strain into a seed medium to be cultured for 36 to 48 h to obtain a first-stage seed, the first-stage seed having $OD_{600}$ of 2 to 3; transferring the first-stage seed at an inoculation quantity of 1%, and culturing for 20 to 24 h to obtain a fermentation seed liquid, the fermentation seed liquid having $OD_{600}$ of 2 to 3; and transferring the fermentation seed liquid to a fermentor at an inoculation quantity of 20 to 25%, and fermenting at a temperature of 35 to 37° C.

* * * * *